United States Patent
Rebollo et al.

(10) Patent No.: US 10,947,276 B2
(45) Date of Patent: Mar. 16, 2021

(54) CELL PENETRATING PEPTIDES WITH IMPROVED INTERNALIZATION PROPERTIES

(71) Applicants: SORBONNE UNIVERSITE, Paris (FR); INSERM (INSTITUT NATIONAL DE LA SANTE ET DE LA RECHERCHE MEDICALE), Paris (FR); CENTRE NATIONAL DE LA RECHERCHE SCIENTIFIQUE, Paris (FR); PEP-THERAPY, Evry (FR)

(72) Inventors: Angelita Rebollo, Paris (FR); Jesus Maria Fominaya Gutierrez, Madrid (ES); Jeronimo Bravo Sicilia, Valencia (ES); Sophie Lebel Binay, Villejuif (FR); Leticia Dominguez Berrocal, Paris (FR)

(73) Assignees: SORBONNE UNIVERSITÉ, Paris (FR); INSERM (INSTITUT NATIONAL DE LA SANTÉ ET DE LA RECHERCHE MEDICALE), Paris (FR); CENTRE NATIONAL DE LA RECHERCHE SCIENTIFIQUE, Paris (FR); PEP-THERAPY, Evry (FR)

( * ) Notice: Subject to any disclaimer, the term of this patent is extended or adjusted under 35 U.S.C. 154(b) by 0 days.

(21) Appl. No.: 16/472,226

(22) PCT Filed: Dec. 18, 2017

(86) PCT No.: PCT/EP2017/083405
§ 371 (c)(1),
(2) Date: Jun. 21, 2019

(87) PCT Pub. No.: WO2018/114863
PCT Pub. Date: Jun. 28, 2018

(65) Prior Publication Data
US 2019/0337985 A1 Nov. 7, 2019

(30) Foreign Application Priority Data

Dec. 22, 2016 (EP) .................................. 16306775

(51) Int. Cl.
| A61K 38/10 | (2006.01) |
| A61K 38/00 | (2006.01) |
| A61P 35/00 | (2006.01) |
| C07K 19/00 | (2006.01) |
| C07K 7/06 | (2006.01) |
| C07K 7/08 | (2006.01) |
| C07K 14/00 | (2006.01) |
| G01N 33/58 | (2006.01) |

(52) U.S. Cl.
CPC ............ *C07K 14/001* (2013.01); *A61P 35/00* (2018.01); *C07K 7/06* (2013.01); *C07K 7/08* (2013.01); *G01N 33/582* (2013.01); *A61K 38/00* (2013.01); *C07K 2319/09* (2013.01); *C07K 2319/10* (2013.01)

(58) Field of Classification Search
CPC ......... A61K 38/00; A61K 38/17; A61P 35/00; C07K 14/001; C07K 14/003; C07K 19/00; C07K 2319/09; C07K 2319/10; C07K 7/06; C07K 7/08; G01N 33/582; G01N 33/68
USPC ..... 530/300, 387.5, 324, 325, 326, 327, 328
See application file for complete search history.

(56) References Cited

U.S. PATENT DOCUMENTS

| 6,387,700 | B1* | 5/2002 | Rice et al. | A61K 48/00 435/320.1 |
| 9,029,636 | B2* | 5/2015 | Wu et al. | C07K 14/415 800/298 |
| 2002/0055174 | A1* | 5/2002 | Rittner et al. | C12N 15/87 530/350 |
| 2017/0015718 | A1 | 1/2017 | Rebollo Garcia et al. | |

FOREIGN PATENT DOCUMENTS

| EP | 2 236 603 | 10/2010 |
| KR | 100883815 | 2/2009 |
| WO | WO 2013/098337 | 7/2013 |
| WO | WO 2015/001045 | 1/2015 |
| WO | WO 2015/022504 | 2/2015 |
| WO | WO 2015/144928 | 10/2015 |
| WO | WO 2016/156536 | 10/2016 |
| WO | WO 2016/156538 | 10/2016 |

OTHER PUBLICATIONS

A0A0L8GIQ1 from UniProt, pp. 1-4. Integrated into UniProtKB/TrEMBL on Nov. 11, 2015. (Year: 2015).*
Pearson WR, "An Introduction to Sequence Similarity ("Homology") Searching," Current Protocols in Bioinformatics, 3.1.1-3.1.8. (Year: 2013).*
Kanduc D, "Homology, similarity, and identity in peptide epitope innnnunodefinition," Journal of Peptide Science, 18: 487-494. (Year: 2012).*
Yampolsky et al., "The Exchangeabiilty of Amino Acids in Proteins," Genetics, 170: 1459-1472. (Year: 2005).*
Park, K. H. et al. "Cell specificity, anti-inflammatory activity, and plausible bactericidal mechanism of designed Trp-rich model antimicrobial peptides" *Biochimica et Biophysica Acta*, 2009, pp. 1193-1203, vol. 1788, No. 5.

(Continued)

*Primary Examiner* — Julie Ha
(74) *Attorney, Agent, or Firm* — Saliwanchik, Lloyd & Eisenschenk

(57) ABSTRACT

A method for delivering a cargo molecule into a cell is described that comprises linking a cargo molecule to a cell penetrating peptide. Chimeric constructs comprising cell penetrating moieties are also provided.

Figure 1:
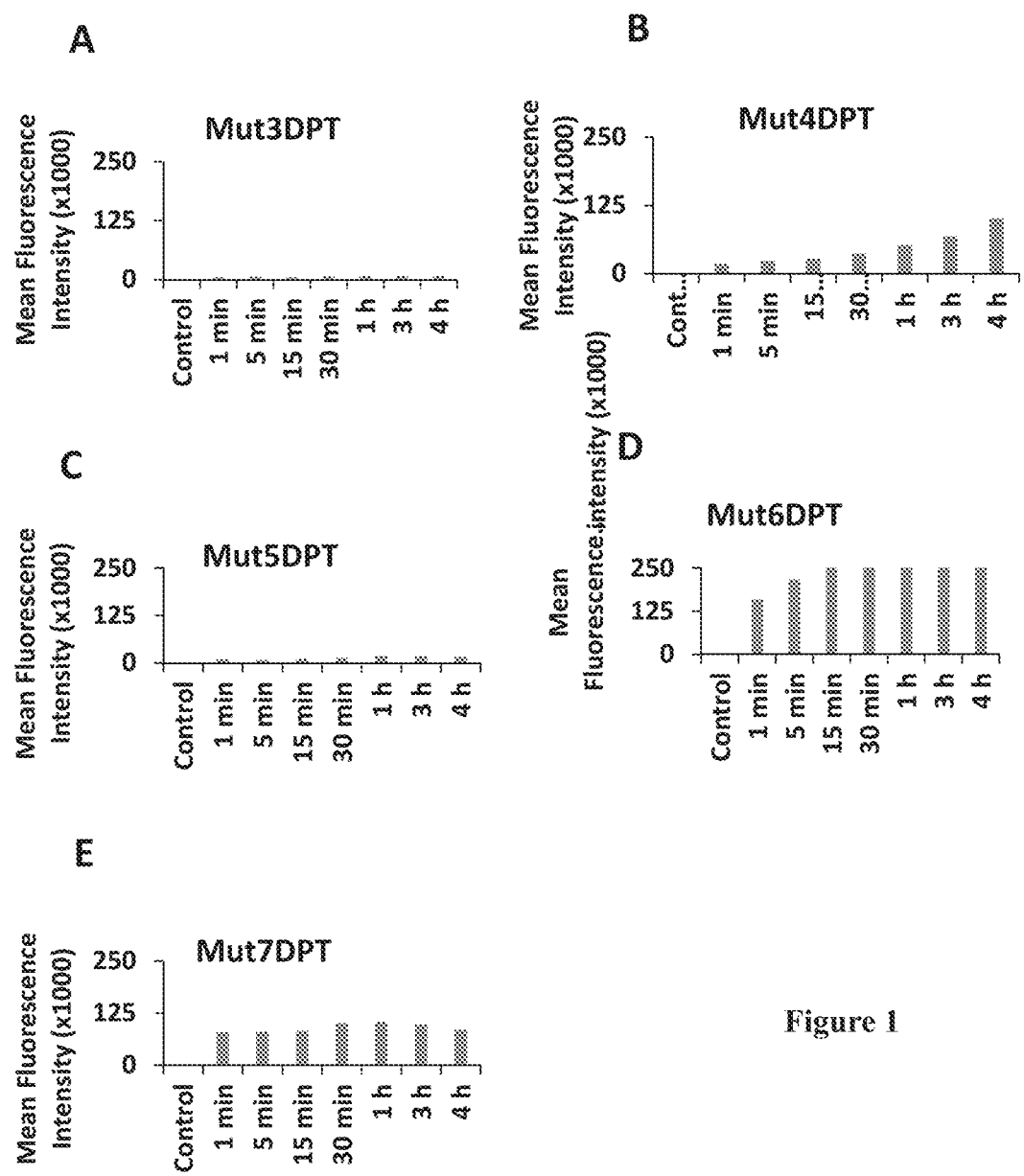

15 Claims, 13 Drawing Sheets
Specification includes a Sequence Listing.

(56) References Cited

OTHER PUBLICATIONS

Bechara, C. et al. "Tryptophan within basic peptide sequences triggers glycosaminoglycan-dependent endocytosis" *The FASEB Journal*, Feb. 1, 2013, pp. 738-749, vol. 27, No. 2.
Written Opinion in International Application No. PCT/EP2017/083405, dated Apr. 17, 2018, pp. 1-9.

* cited by examiner

CELL PENETRATING PEPTIDES WITH IMPROVED INTERNALIZATION PROPERTIES

CROSS-REFERENCE TO RELATED APPLICATION

This application is the U.S. national stage application of International Patent Application No. PCT/EP2017/083405, filed Dec. 18, 2017.

The Sequence Listing for this application is labeled "Seq-List.txt" which was created on Jun. 19, 2019 and is 17 KB. The entire content of the sequence listing is incorporated herein by reference in its entirety.

The present invention relates to novel cell penetrating peptides which have been designed for intracellular delivery of various cargos. The invention further relates to chimeric polypeptides which comprise such cell penetrating peptide linked to a peptide of interest.

TECHNICAL BACKGROUND

In the field of biomedicine and engineered carrier systems, cell penetrating peptides (CPPs) have been developed as a promising tool for therapeutic and diagnostic applications. CPPs are widely used for intracellular delivery of various cargos, including small molecule drugs, peptides, proteins, genes and nanoparticles. However, one of the limitations for the therapeutic use of CPPs is the susceptibility to degradation by proteases. To overcome this issue, different types of strategies have been designed, including substitution of L with D amino acids, cyclization and helix stabilization by peptide stapling, as well as shielding approach.

CPPs are able to cross cell membranes and deliver macromolecules. However the cellular requirements for efficient internalization are not fully understood.

There is still a need for designing CPPs with an improved capacity of cell internalization.

SUMMARY OF THE INVENTION

A subject of the invention is a construct comprising a cell penetrating moiety consisting of KKKKKWKKWKKK (SEQ ID NO: 7) or KKKKKWKKW (SEQ ID NO: 9), linked to a cargo molecule.

The cargo molecule may be selected from the group consisting of a peptide, a protein, a nucleic acid, and a small molecule.

In another aspect of the invention, it is provided a construct which is a chimeric polypeptide comprising i) a cell penetrating moiety consisting of RRWRRWRRWRR (SEQ ID NO:6) or RRWRRWRRW (SEQ ID NO:8), fused to ii) a cargo molecule that is a peptide.

Preferably the construct is a chimeric polypeptide comprising a peptide as the cargo molecule, which chimeric polypeptide comprises no more than 100 amino acids, preferably no more than 60 amino acids, still preferably no more than 30 amino acids.

Still preferably, the cell penetrating moiety is fused to at least one nuclear localization amino acid sequence. In a still preferred embodiment, the nuclear localization amino acid sequence is bipartite and comprises or consists of a) sequence RKR fused at N-terminus of the cell penetrating moiety sequence and b) sequence PKKKKLD (SEQ ID NO: 26) fused at C-terminus of the cell penetrating moiety sequence.

In a preferred aspect, the construct of the invention is a chimeric polypeptide comprising a pro-apoptotic peptide as the cargo molecule.

A preferred construct comprises i) sequence RKR-KKKKKWKKW-PKKKKLD (SEQ ID NO: 27, also designated NLS18) or RKR-KKKKKWKKWKKK-PKKKKLD (SEQ ID NO: 28, also designated NLS23), which sequence is fused to ii) a pro-apoptotic peptide.

The still preferred construct is a chimeric polypeptide that comprises or consists of a sequence selected from the group consisting of:

```
RKR-KKKKKWKKW-PKKKKLD-RLQLVEFSAFVEPPDAVD
(SEQ ID NO: 29, also designated NLS18-TEAD);

RKR-KKKKKWKKWKKK-PKKKKLD-RLQLVEFSAFVEPPDAVD
(SEQ ID NO: 30, also NLS23-TEAD);

RKR-KKKKKWKKW-PKKKKLD-KTANVPQTVPMRLRKLPD
(SEQ ID NO: 31, also NLS18-YAP);
and

RKR-KKKKKWKKWKKK-PKKKKLD-KTANVPQTVPMRLRKLPD
(SEQ ID NO: 32, also NLS23-YAP).
```

LEGENDS TO THE FIGURES

FIG. 1. Time-dependent penetration of new generated shuttles.

MCF-7 or Jurkat cell lines were cultured in the presence or in the absence of Mut3DPT (Panel A), Mut4DPT (Panel B), Mut5DPT (Panel C), Mut6DPT (Panel D) or Mut7DPT (Panel E) at 50 µM for different periods of time. The intensity of the FITC fluorescence due to the shuttle internalization was measured by FACS. The results presented in the figure correspond to MCF-7 cells. Similar results were obtained using Jurkat cell line.

Figure 2:
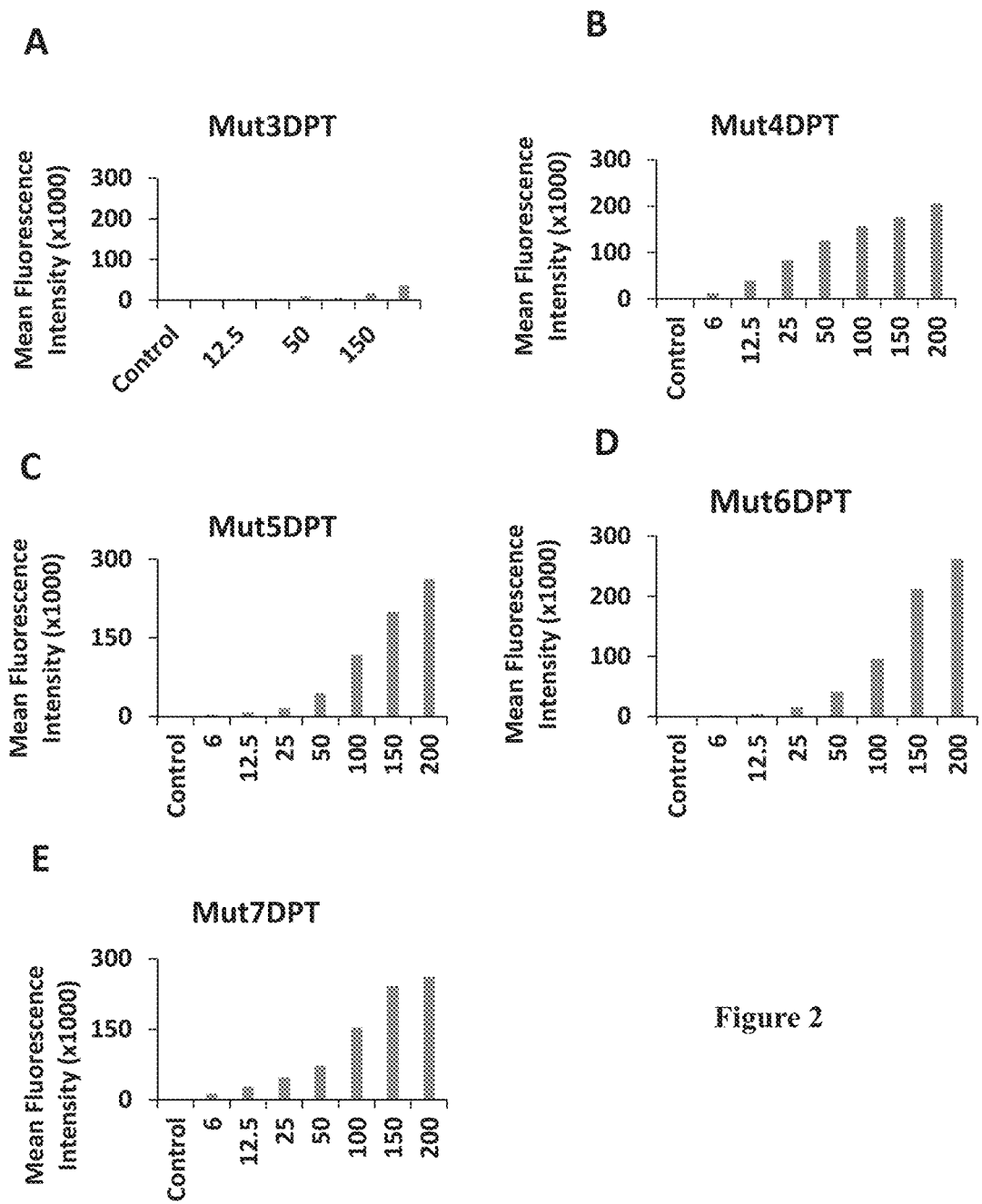

FIG. 2. Concentration-dependent penetration of new generated shuttles.

MCF-7 or Jurkat cell lines were cultured in the presence or in the absence of Mut3DPT (Panel A), Mut4DPT (Panel B), Mut5DPT (Panel C), Mut6DPT (Panel D) or Mut7DPT (Panel E) at different concentrations for 4 h. The intensity of the FITC fluorescence due to the shuttle internalization was measured by FACS. The results presented in the figure correspond to MCF-7 cells. Similar results were obtained using Jurkat cell line.

Figure 3:
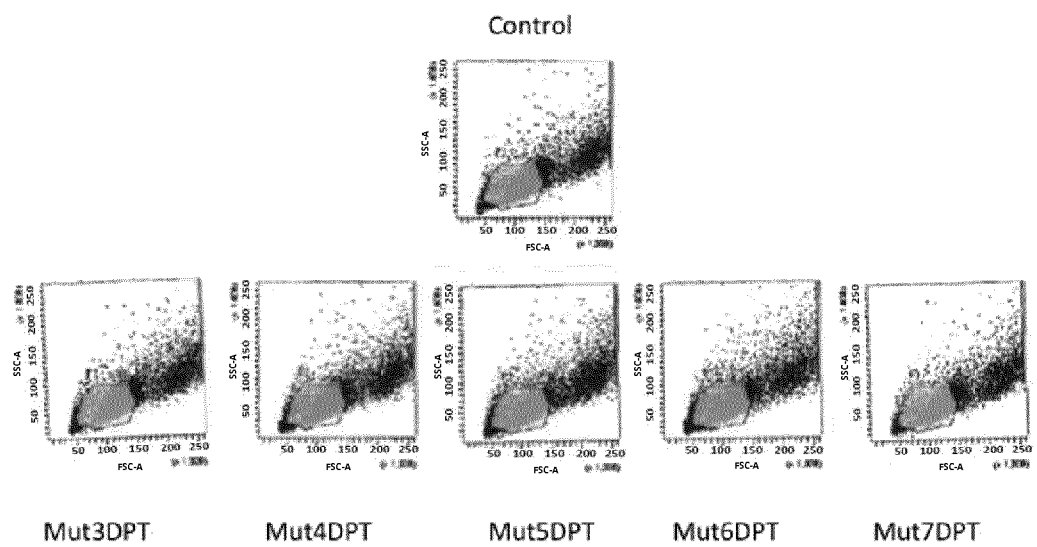

FIG. 3. Effect of the peptides on toxicity.

MCF-7 or Jurkat cells were cultured in the presence or in the absence of 100 µM of the peptides and analyzed by FACS for detection of toxicity. The results presented on the Figure correspond to MCF-7. Similar results were obtained using Jurkat cells.

Figure 4:
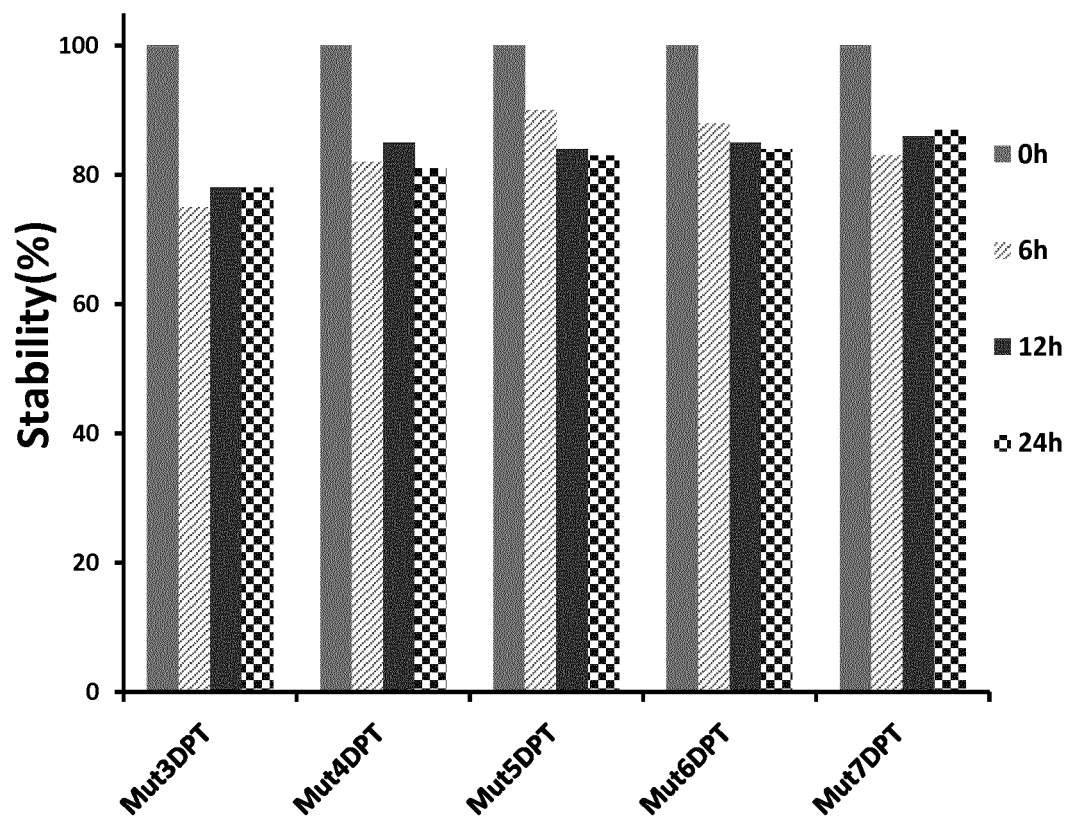

FIG. 4. Stability of the new generated shuttles in human serum.

A) Mut3DPT, Mut4DPT, Mut5DPT, Mut6DPT and Mut7DPT peptides were incubated at 37° C. in human serum for different periods of time and their integrity (percentage of intact peptide) were analyzed by mass spectrometry. Similar results were obtained in two independent experiments.

Figure 5:
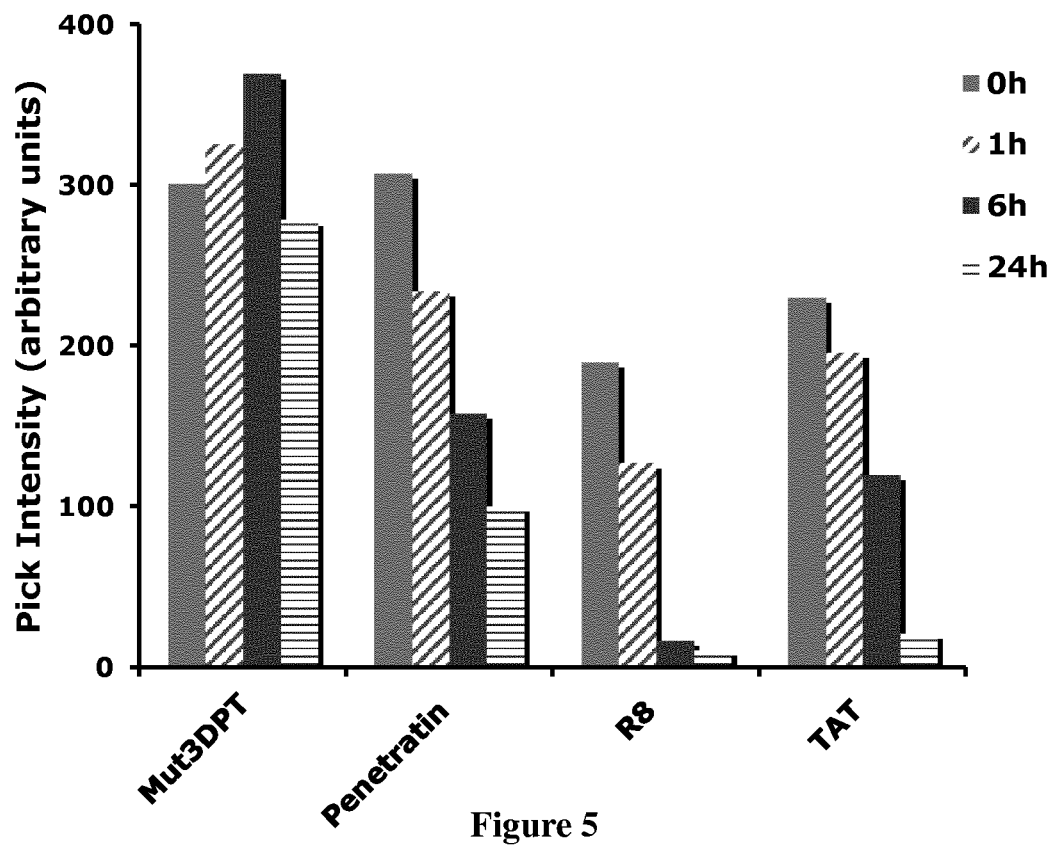

FIG. 5. Mut3DPT, Tat, Penetratin and R8 were treated and analyzed as above. The stability is referred to the intensity of the peaks.

Figure 6:
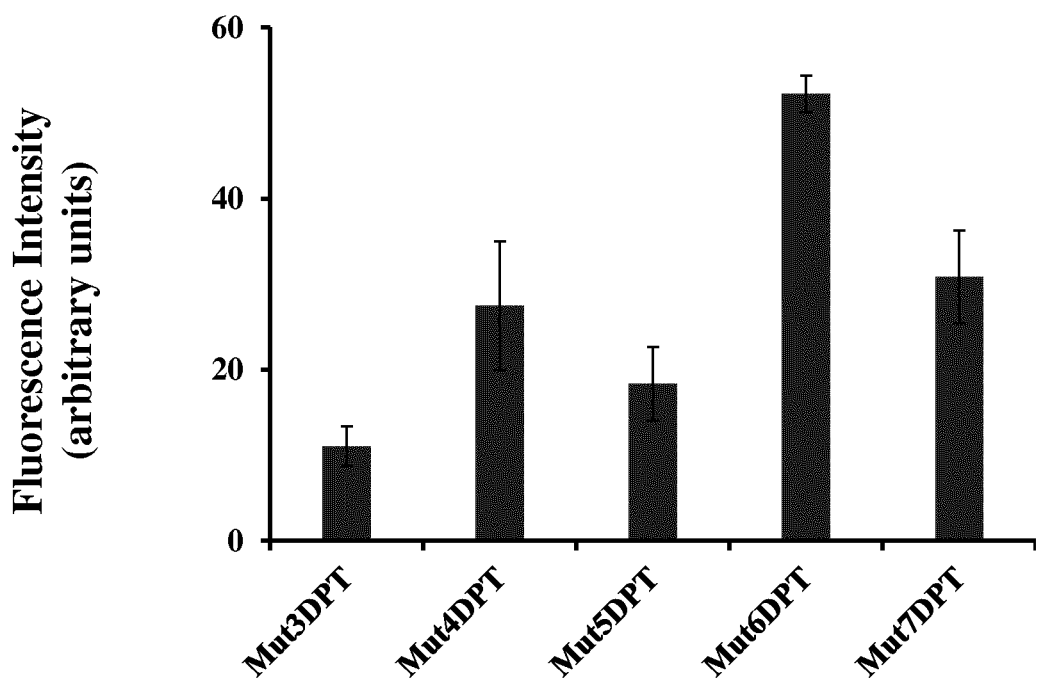
Figure 6:
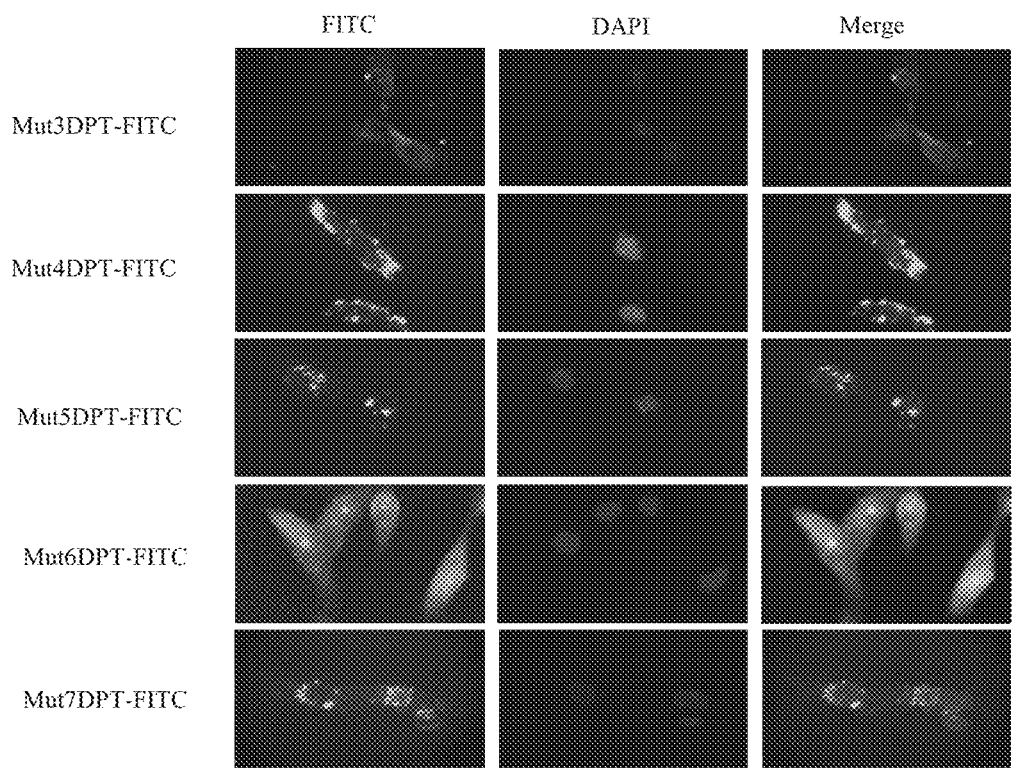

FIG. 6. Intracellular localization of FITC-labelled shuttles.

A) MCF-7 cells were grown on coverslips and incubated 1 h at 37° C. with 25 µM of FITC-labelled peptides. Cells were washed 3 times with PBS, fixed with 4% paraphormaldeyde (PFA) and analyzed by fluorescence microscopy. Quantification of the microscopy images is shown. B) MCF7 were grown as above and incubated for different periods of time at 37° C. with 25 µM of FITC-labelled shuttles. Cells were treated as above and analyzed by fluorescence microscopy.

Figure 7:
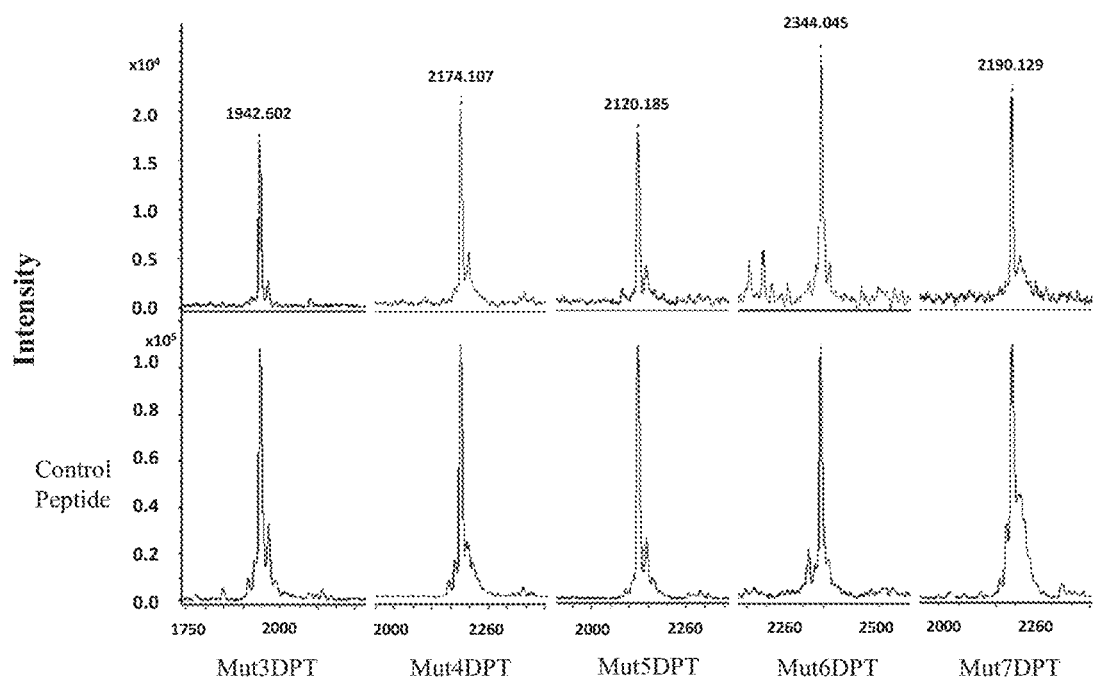

FIG. 7. Intracellular detection by mass spectrometry (MS) of the shuttles.

MCF-7 cells were cultured 4 h with 100 µM of each shuttle. After several washing steps, they were lysed and the extracts centrifuged. The intracellular peptide was detected by MS. Pure peptide was used as a control of molecular weight.

Figure 8:
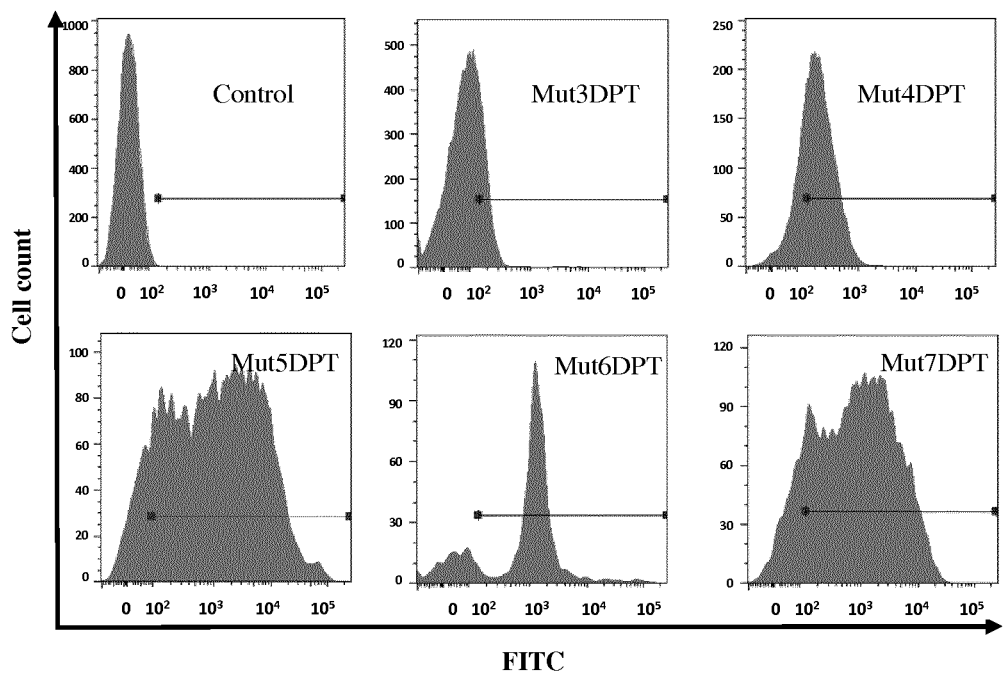
Figure 8:
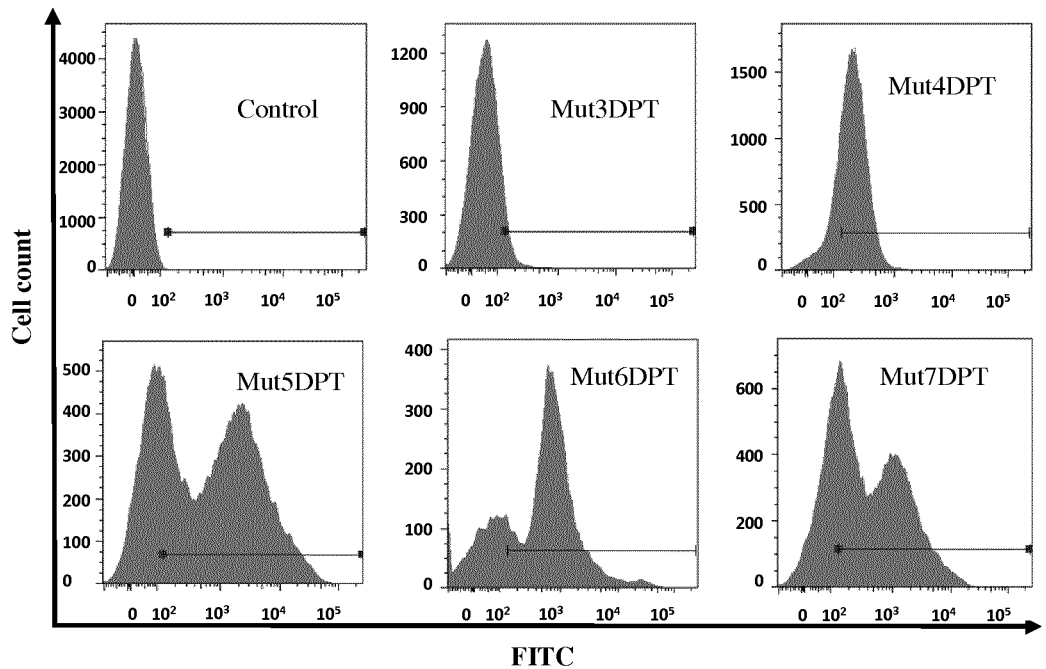

FIG. 8. Internalization of FITC-labelled shuttles on healthy and tumoral primary B cells.

A) B cells were isolated (anti-hCD19-APC antibody) from peripheral blood mononuclear cells (PBMC) of healthy donors (HD) or B) chronic lymphocytic leukemia (CLL) patients. Cells were incubated 4 h with 100 µM of the FITC-labelled shuttles. The mean fluorescence intensity was detected by flow cytometry. Non treated cells were used as control.

Figure 9:
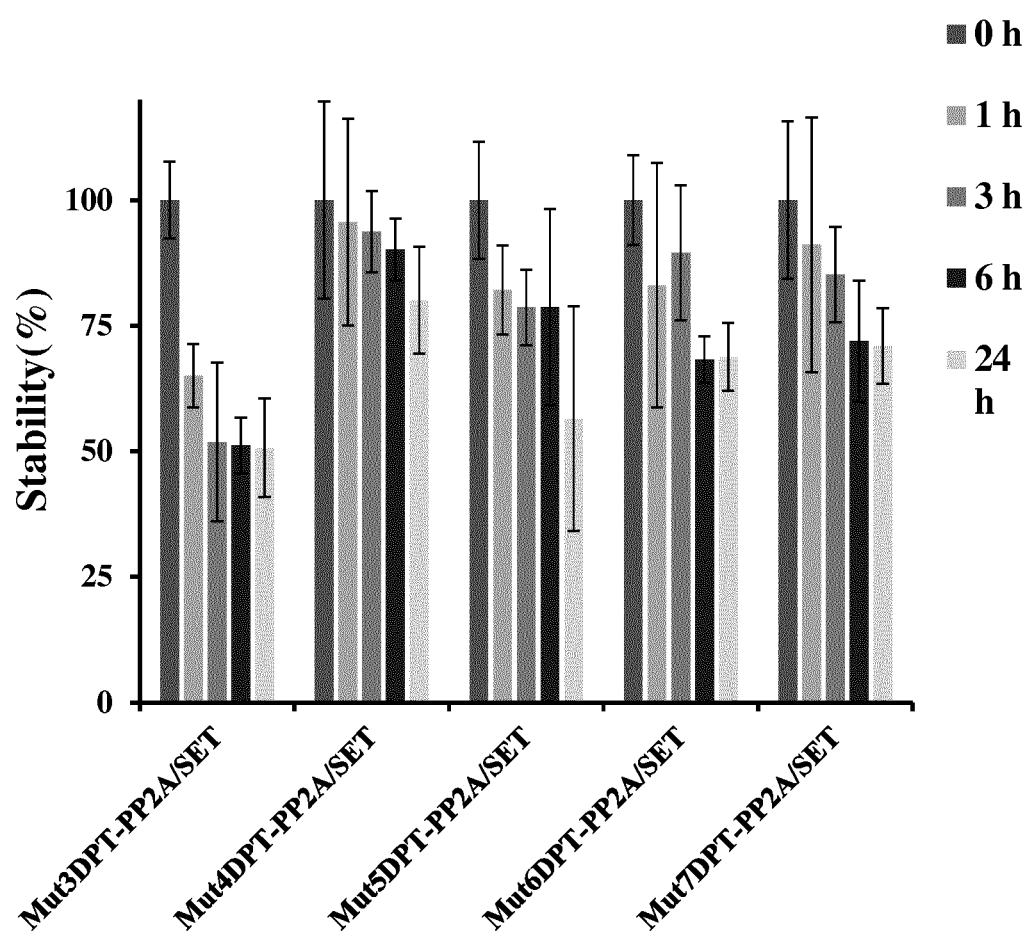

FIG. 9. Stability in human serum of the shuttles associated to a cargo (PP2A/SET binding site).

The shuttles associated to the cargo PP2A/SET of sequence ETVTLLVALKVRYRERIT (SEQ ID NO:33) were incubated at 37° C. in human serum for different periods of time and their integrity (percentage of intact peptide) was analyzed by mass spectrometry (MS). Measurements were performed in triplicate and standard deviation is shown.

Figure 10:
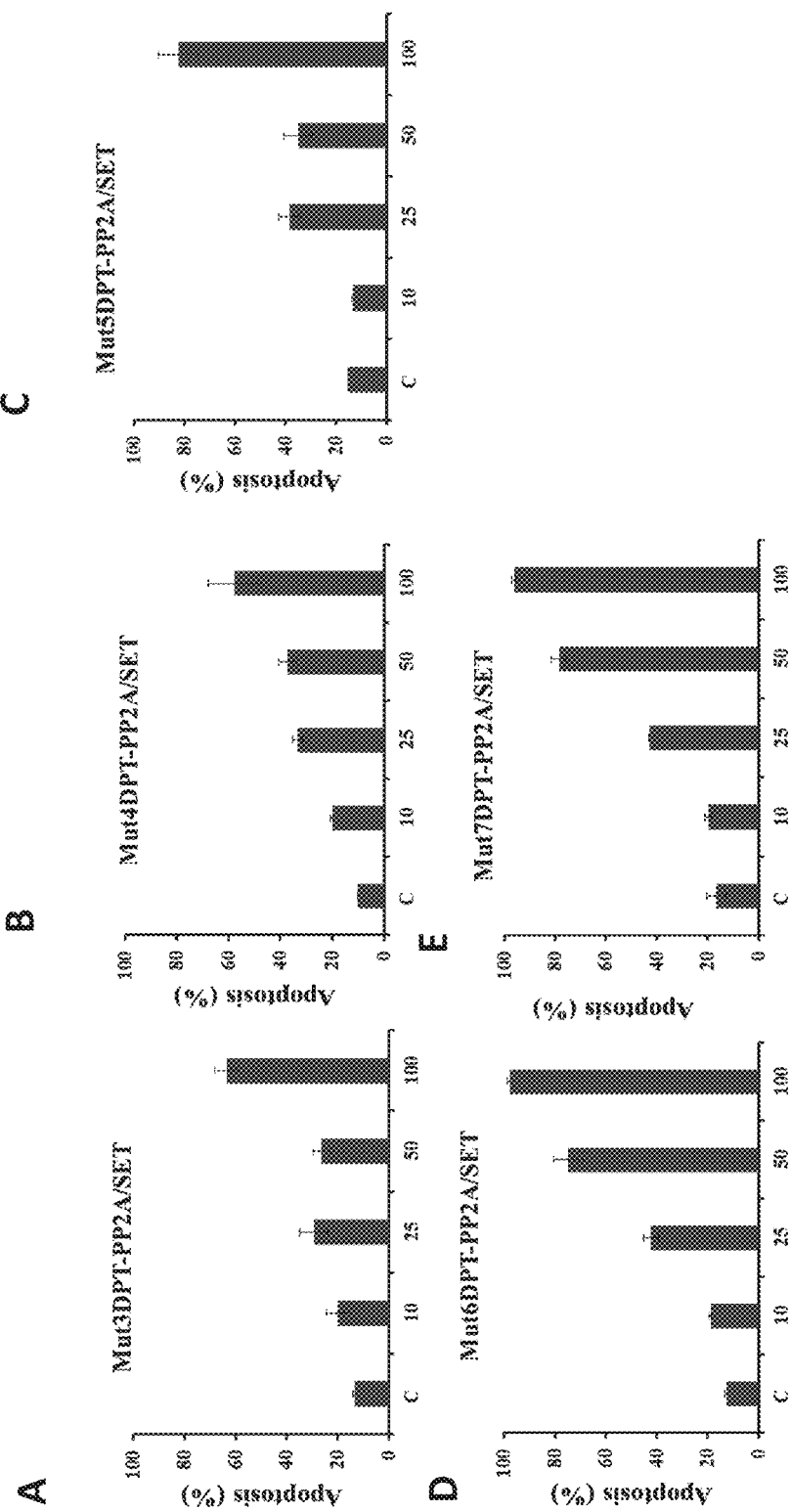

FIG. 10. Detection of apoptosis induced by the shuttles associated to a cargo.

MCF-7 cells were cultured in the presence of different concentrations of peptides associated to the cargo (PP2A/SET binding site of sequence ETVTLLVALKVRYRERIT, SEQ ID NO:33) for 24 h (Mut3DPT-PP2A/SET, Panel A; Mut4DPT-PP2A/SET, Panel B; Mut5DPT-PP2A/SET, Panel C; Mut6DPT-PP2A/SET, Panel D; Mut7DPT-PP2A/SET, Panel E). Apoptosis was estimated by Annexin-V-FITC staining. Non treated cells were used as control. Standard deviation is shown.

Figure 11:
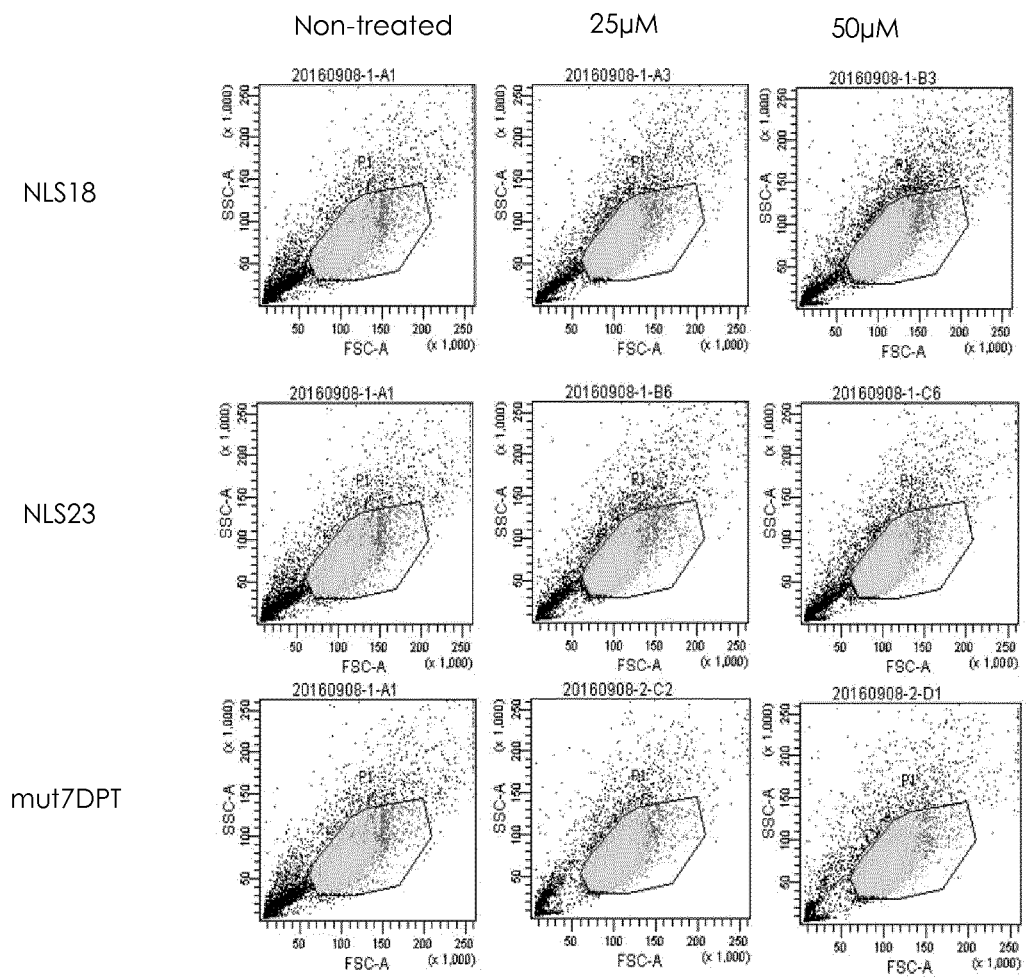

FIG. 11. Analysis of toxicity of NLS18 and NLS23.

MDA-MB231 cells ($6\times10^4$ cells/ml) were incubated 4 h with two different concentrations of peptide. Toxicity was analyzed by flow cytometry. The sequence of NLS18 is RKR-KKKKKWKKW-PKKKKLD (SEQ ID NO:27) and the sequence of NLS23 is RKR-KKKKKWKKWKKK-PKKKKLD (SEQ ID NO:28). Non treated cells were used as a control.

Figure 12:
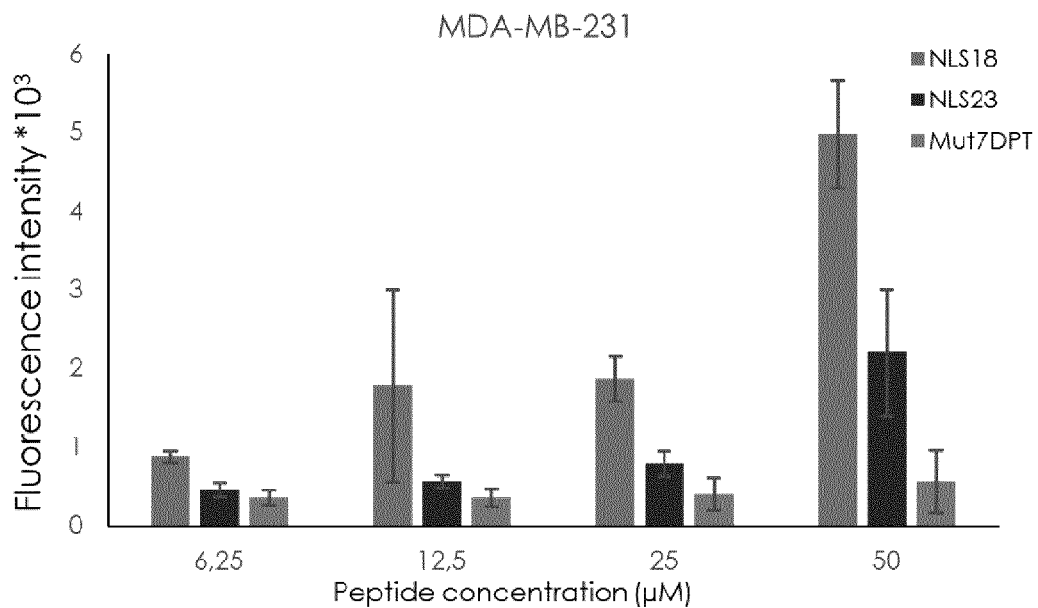

FIG. 12. Concentration-dependent penetration of FITC-labelled shuttles.

MDA-MB231 cells ($5\times10^4$ cells/ml) were incubated 4 h with different concentrations of FITC-labelled nuclear shuttles. The fluorescence intensity was detected by flow cytometry and compared to cells treated with mut7DPT control peptide. Standard deviation is shown.

Figure 13:
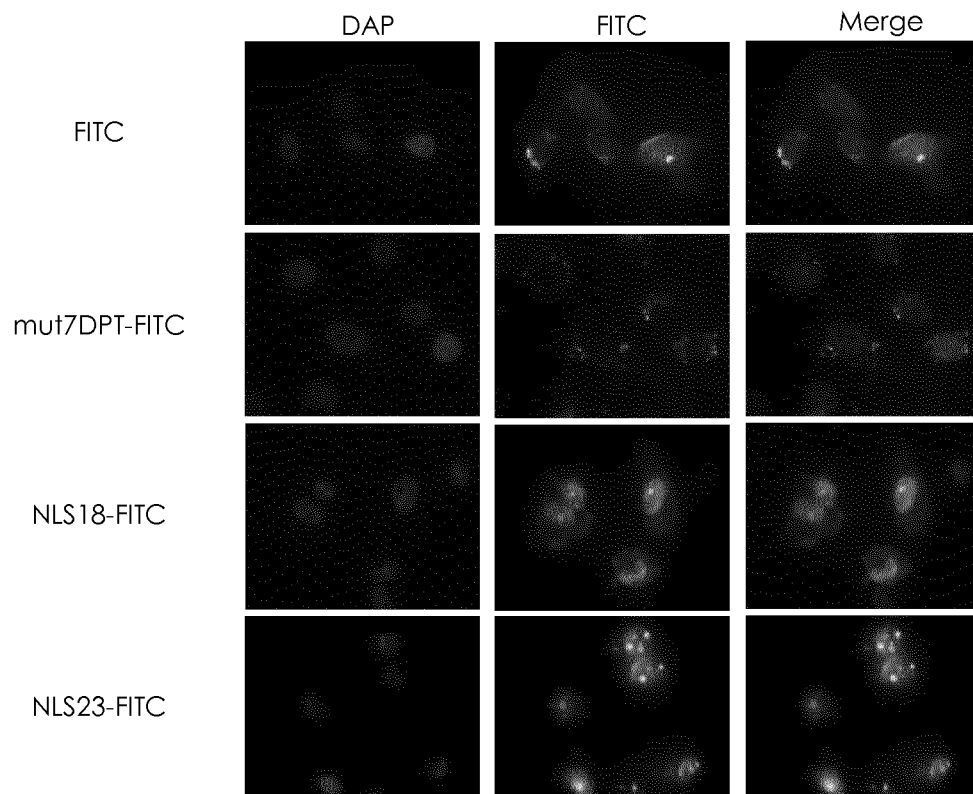

FIG. 13 Intracellular localization of FITC-labelled shuttles.

MDA-MB231 cells ($3\times10^4$ cells/ml) were grown on cover slips and incubated 4 h with 30 µM of FITC-labelled peptides. Cells were washed 3 times with PBS, fixed with 4% paraformaldeyde (PFA) and analyzed by fluorescence microscopy. Cells treated with mut7DPT-FITC were used as control.

Figure 14:
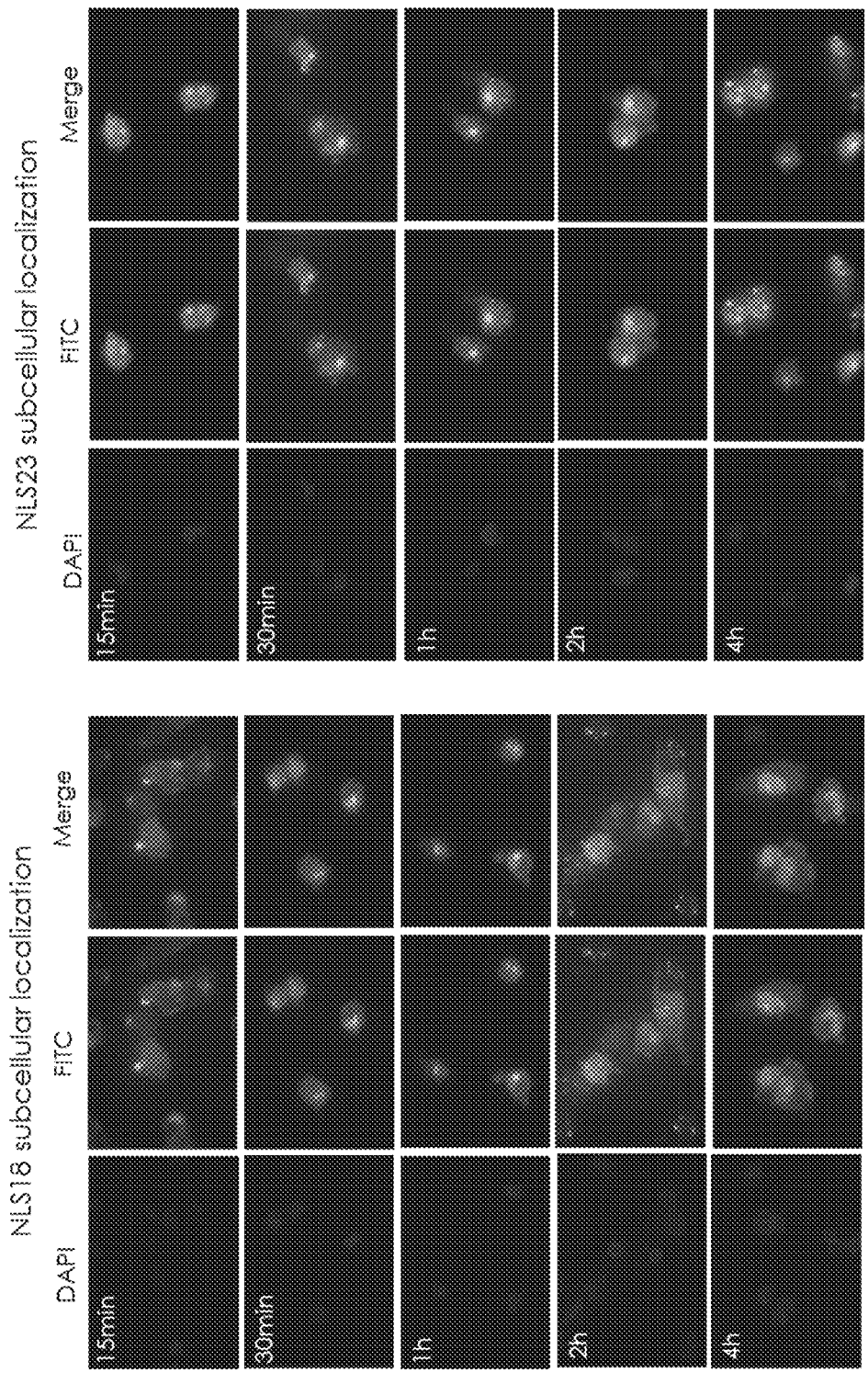

FIG. 14. Time-dependent nuclear localization of FITC-labelled shuttles.

MDA-MB231 cells ($3\times10^4$ cells/ml) were grown on cover slips and incubated with 30 µM of peptide for different periods of time. Cells were washed 3 times with PBS, fixed with 4% PFA and analyzed by fluorescence microscopy.

Figure 15:
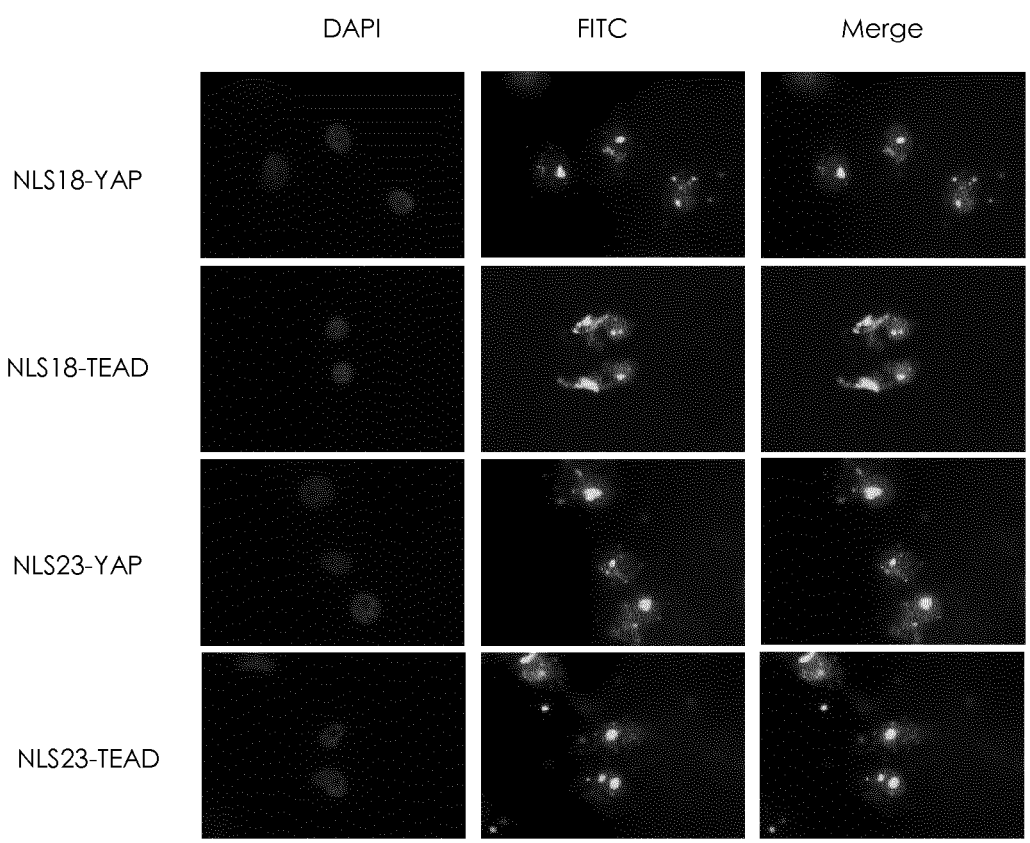

FIG. 15. Intracellular localization of FITC-labelled shuttles associated to a cargo.

MDA-MB231 cells ($3\times10^4$ cells/ml) were incubated in cover slips for 3 h with 15 µM of the FITC-labelled peptides associated to a cargo (TEAD or YAP peptides). Cells were washed 3 times with PBS, fixed with 4% PFA and analyzed by fluorescence microscopy.

Figure 16:
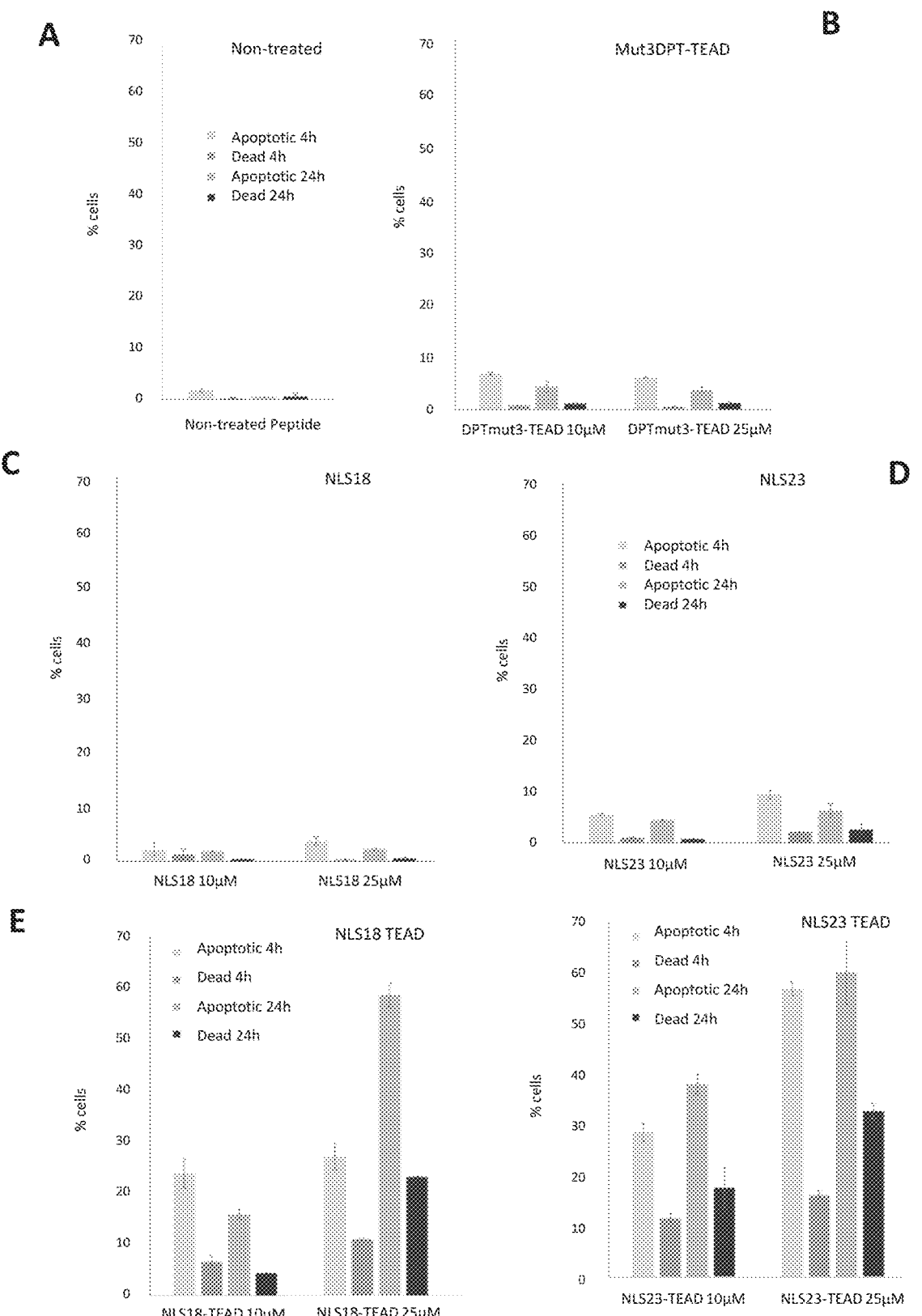

FIG. 16. Detection of apoptosis induced by the nuclear localization shuttles associated to a cargo.

MDA-MB231 cells ($5\times10^4$ cells/ml) were cultured in the presence of different concentrations of shuttles or nuclear localization shuttles associated to the cargo TEAD for 4h or 24h (Non-treated, Panel A; Mut3DPT-TEAD, Panel B; NLS18, Panel C; NLS23, Panel D; NLS18 TEAD, Panel E, NLS23 TEAD, Panel F). Apoptosis was estimated by Annexin V-FITC staining. Cells treated with shuttle without cargo or nuclear localisation signal (NLS) were used as control. Standard deviation is shown.

DETAILED DESCRIPTION OF THE INVENTION

The inventors have now shown that internalization of CPPs varies among peptides with different tryptophan (Trp, W) content and backbone spacing, also showing that uptake efficiency is higher for the peptides with three tryptophans in the middle but not when added to the N-terminus. Taken together, these results prove that tryptophan content can affect both CPP uptake mechanism and efficiency.

In addition, peptides with Trp residues adopt a predominantly a helix structure increasing the quantity of internalized peptide. It has been also shown that arginine residues are also efficient in eliciting cellular internalization of proteins.

The CPPs of the invention show various improved properties, such as proteolysis resistance as well as increase of penetration. Improvement of in vivo pharmacokinetic parameters is then made possible. Additionally, increased serum stability and internalization allow dose reduction and, consequently, translate into several advantages, including cost reduction and decrease of potential undesired secondary effects as well as increasing the therapeutic index of the CPP-cargo.

It is herein provided a method for delivering a cargo molecule into a cell, which method comprises linking said cargo (poly)peptide molecule to a cell penetrating peptide consisting of an amino acid sequence of formula (I) $\psi X_1\psi W\psi W\psi X_2$ (SEQ ID NO:1) formula (II) $\psi X_1\psi W\psi W$ (SEQ ID NO:2), wherein $\psi$ represents amino acids KK or RR, X1 is K or W, $X_2$ is K or vacant, or formula (III) $X_3$KKWKIKWWX$_4$ (SEQ ID NO:3), wherein $X_3$ is V or vacant, and $X_4$ is IKI or vacant.

In a preferred embodiment, said cargo molecule is a (poly)peptide. In a still preferred embodiment, the method comprises fusing said cargo molecule to said penetrating peptide.

The constructs which comprise the cell penetrating peptide as defined herein, linked to a cargo molecule are part of the present invention.

The cargo molecule may be e.g. a peptide, a protein, a nucleic acid, and a small molecule. In a particular embodiment, the cargo molecule is a therapeutic agent. The construct may then be used as a medicament.

In another particular embodiment, the cargo molecule is a labelling agent. The construct may then be used in diagnostics.

The invention more particularly provides a (poly)peptide of no more than 100 amino acids, preferably no more than 60 amino acids, still preferably no more than 30 amino acids, comprising a cell penetrating moiety consisting of an amino acid sequence of formula (I) $\psi X_1 \psi W \psi W \psi X_2$ (SEQ ID NO:1), formula (II) $\psi X_1 \psi W \psi W$ (SEQ ID NO:2), wherein $\psi$ represents amino acids KK or RR, $X_1$ is K or W, $X_2$ is K or vacant, or formula (III) $X_3 KKWKIKWWX_4$ (SEQ ID NO:3), wherein $X_3$ is V or vacant, and $X_4$ is IKI or vacant.

The (poly)peptide preferably comprises, or consists of, an amino acid sequence selected from the group consisting of RRWRRWRRWRR (SEQ ID NO:6, designated "Mut6DPT"), RRWRRWRRW (SEQ ID NO:8), KKKKKWKKWKKK (SEQ ID NO:7, designated "Mut7DPT"), KKKKKWKKW (SEQ ID NO:9), KKWKKWKKWKK (SEQ ID NO:5, designated "Mut5DPT"), KKWKKWKKW (SEQ ID NO:10), VKKWKIKWWIKI ((SEQ ID NO:4, designated "Mut4DPT") and VKKWKIKWW (SEQ ID NO: 11).

In a particular embodiment, the (poly)peptide is a chimeric polypeptide further comprising a pro-apoptotic peptide. Such polypeptide is useful in treating a hyperproliferative disorder, preferably a tumor.

DEFINITIONS

The term "patient" refers to a human or non human animal, preferably a mammal, including male, female, adult and children.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder. Prophylactic treatment refers to any of: halting the onset, reducing the risk of development, reducing the incidence, delaying the onset, reducing the development, as well as increasing the time to onset of symptoms of a particular disorder.

The term "penetrating peptide" or "cell-penetrating peptide" (or "CPP") or "shuttle peptide", as used interchangeably, means that the peptide is able to translocate into cells without causing substantial membrane damage, and can be used as a vector of other molecules (designated as "cargos") when linked to them. The CPP, as shown herein, have the capability of inducing cell penetration of a peptide fused to the CPP within 30%, 40%, 50%, 60%, 70%, 80%, 90%, or 100% of cells of a given cell culture population, including all integers in between, and allow macromolecular translocation within multiple tissues in vivo upon systemic administration. A cell-penetrating peptide may also refer to a peptide which, when brought into contact with a cell under appropriate conditions, passes from the external environment in the intracellular environment. This property may be assessed by various methods known by the skilled person. The cell penetrating moiety can be fused to a sequence directing the construct to a cellular organelle such as mitochondria or nucleus. Preferably, the cell penetrating moiety is fused to a nuclear localization sequence, which can be monopartite or bipartite. Advantageously, the nuclear localization amino acid sequence is bipartite and comprises or consists of a) sequence RKR fused at N-terminus of the cell penetrating moiety sequence and b) sequence PKKKKLD (SEQ ID NO: 26) fused at C-terminus of the cell penetrating moiety sequence. As an example, the cell penetrating moiety fused to a NLS sequence is selected in the group comprising or consisting of RKR-KKKKKWKKW-PKKKKLD (SEQ ID NO: 27, also designated NLS18) and RKR-KKKKKWKKWKKK-PKKKKLD (SEQ ID NO: 28, also designated NLS23).

The term "cargo" refers to a peptide, protein, a nucleic acid, a small molecule or macromolecule of interest, which is to be transferred into a cell. It may be a pro-apoptotic agent (such as a pro-apoptotic peptide), an immunogenic peptide, a tumor antigen, a cytotoxic agent (such as a cytotoxic peptide), for instance. In a particular embodiment, the cargo may be an antibody or a fragment thereof, such as Fab or scFv fragments. Aptamers, nanobodies or alphabodies may also be used as a cargo. Nanobodies are antibody fragments consisting of a single monomeric variable antibody domain. Alphabodies (developed by Compix N.V) are small 10 kDa proteins engineered to bind to a variety of antigens. In still another embodiment, the cargo may be an oligonucleotide, including DNA, RNA, or siRNA.

The cargo may be selected for its properties for treating an inflammation, an infection, a metabolic condition or a tumor.

It may also be a labelling agent, useful as a tracer or probe, e.g. for diagnosis or in vivo or ex vivo imaging. For instance it may be a fluorochrome, fluorophore, etc.

A sequence that derives from" or "is derived from" a reference sequence is a peptide sequence that is longer than the reference sequence, or is a homologous sequence, as defined herein.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented.

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilio-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

By "substituted" or "modified" the present invention includes those amino acids that have been altered or modified from naturally occurring amino acids.

As such, it should be understood that in the context of the present invention, a conservative substitution is recognized in the art as a substitution of one amino acid for another amino acid that has similar properties. Examples of conservative substitutions are set out in the Table 1 below:

TABLE 1

Conservative Substitutions I

| SIDE CHAIN CHARACTERISTIC | AMINO ACID |
|---|---|
| Non-polar | G A P I L V |
| Polar-uncharged | C S T M N Q |
| Polar-charged | D E K R |
| Aromatic | H F W Y |
| Other | N Q D E |

Alternatively, conservative amino acids can be grouped as described in Lehninger, 1975, as set out in Table 2, immediately below.

TABLE 2

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

As still another alternative, exemplary conservative substitutions are set out in Table 3, immediately below.

TABLE 3

Conservative Substitutions III

| Original Residue | Exemplary Substitution |
|---|---|
| Ala (A) | Val (V), Leu (L), Ile (I) |
| Arg (R) | Lys (K), Gln (Q), Asn (N) |
| Asn (N) | Gln (Q), His (H), Lys (K), Arg (R) |
| Asp (D) | Glu (E) |
| Cys (C) | Ser (S) |
| Gln (Q) | Asn (N) |
| Glu (E) | Asp (D) |
| His (H) | Asn (N), Gln (Q), Lys (K), Arg (R) |
| Ile (I) | Leu (L), Val (V), Met (M), Ala (A), Phe (F) |
| Leu (L) | Ile (I), Val (V), Met (M), Ala (A), Phe (F) |
| Lys (K) | Arg (R), Gln (Q), Asn (N) |
| Met (M) | Leu (L), Phe (F), Ile (I) |
| Phe (F) | Leu (L), Val (V), Ile (I), Ala (A) |
| Pro (P) | Gly (G) |
| Ser (S) | Thr (T) |
| Thr (T) | Ser (S) |
| Trp (W) | Tyr (T) |
| Tyr (Y) | Trp (W), Phe (F), Thr (T), Ser (S) |
| Val (V) | Ile (I), Leu (L), Met (M), Phe (F), Ala (A) |

Chimeric Constructs:

The novel CPP is chemically linked, or fused, to a cargo molecule of interest. In particular embodiments, the cargo is linked to one, two, three or more cell-penetrating peptides. The cargo is advantageously linked to the C-terminus of the cell-penetrating peptide.

A linker may be used, which may be of any type. For instance it may be a peptide or a carboxylic acid chain. The linker may contain diverse functional groups, in particular it may be functionalized with maleimide (sulfhydral reactive) and succinimidyl ester (NHS) or isothiocyanate (ITC) groups that react with amines. In a preferred embodiment, it is herein described (poly)peptides which are chimeric constructs, comprising a novel CPP as described herein, fused to the N-terminal and/or C-terminal end(s) of a cargo, which preferably is a pro-apoptotic peptide. The length of the chimeric (poly)peptide is not critical to the invention as long as it is functional. However it is preferably no more than 100 amino acids, preferably no more than 90, 80, 70, 60 amino acids, still preferably less no more than 50, 40, 30, or 25 amino acids. It may preferably have a length comprised between 17 to 80 amino acids, preferably between 20 to 70 amino acids, still preferably between 23 to 40 amino acids. Unless otherwise stated, the terms "peptide", "polypeptide", or "(poly)peptide" are used indifferently.

The (poly)peptide may further comprise protein/peptide moieties including those which allow the purification, detection, immobilization etc.

These moieties may be selected from: a labeling moiety such as a fluorescent protein (GFP and its derivatives, BFP and YFP), a reporter moiety such as an enzyme tag (luciferase, alkaline phosphatase, glutathione-S-transferase (GST), β-galactosidase), a binding moiety such as an epitope tag (polyHis6, FLAG, HA, myc.), a DNA-binding domain, a hormone-binding domain, a poly-lysine tag for immobilization onto a support, a stabilization moiety, and a targeting moiety for addressing the chimeric protein to a specific cell type.

In addition, such moieties may be separated from the cargo by a linker which is long enough to avoid interactions. The linker may also comprise a recognition site for a protease, for example, for removing affinity tags and stabilization moieties from the purified chimeric protein according to the present invention.

In one embodiment, the chimeric (poly)peptide comprises a cargo linked to at least one cell-penetrating peptide. In particular embodiments, the cargo is linked to two, three or more cell-penetrating peptides. The cargo is advantageously fused to the C-terminus of the cell-penetrating peptide.

Pro-Apoptotic Peptides

The pro-apoptotic peptide typically induces cell apoptosis and is useful for inhibiting cell proliferation in vitro and in vivo, in particular for treating a hyperproliferative disorder, such as cancer. Advantageously, the pro-apoptotic peptides induce cell apoptosis, in vitro and/or in vivo.

Assays for determining if a molecule, for instance a peptide, induces cell apoptosis are well-known in the art and include, for instance, incubating cells with the candidate peptide and determining if apoptosis is induced by said candidate peptide, e.g. by Annexin V and PI labelling of cells and identifying as apoptotic cells, those being Annexin $V^+$ and $PI^-$.

The pro-apoptotic peptide typically has a length comprised between 18 to 80 amino acids, preferably between 18 to 70 amino acids, still preferably between 18 to 40 amino acids, still preferably between 18 and 30 amino acids.

A number of pro-apoptotic peptides are known in the art.

In a particular embodiment, the pro-apoptotic peptide is derived from or consists of a portion of PP2A or SET that binds a SET or PP2A protein respectively, as described in international patent application WO2016/156536.

More particularly, the pro-apoptotic peptide may comprise or consist of sequence ETVTLLVALKVRYRERIT (SEQ ID NO:12, designated as "PP2Ach-S2" or "PP2A/SET") or PSSKSTEIKWKSGKDLTKRSSQ (SEQ ID NO:13, designated as "SET2h-S3"), or a proteolysis-resistant peptide deriving from said pro-apoptotic peptide by one or more chemical modifications, or a substantially homologous peptide, preferably deriving from SEQ ID NO: 12 or 13 by one or more conservative substitutions.

In a particular embodiment, the (poly)peptide comprises or consists of RRWRRWRRWRR-ETVTLLVALKVRYRERIT (SEQ ID NO:14, designated as "Mut6DPT-PP2Ach-S2" or "Mut6DPT-PP2A/SET"), RRWRRWRRWRR-PSSKSTEIKWKSGKDLTKRSSQ (SEQ ID NO:15, designated as "Mut6DPT-SET2h-S3"), KKKKKWKKWKKK-ETVTLLVALKVRYRERIT (SEQ ID NO:16, designated as "Mut7DPT-PP2Ach-S2" or "Mut7-PP2A/SET"), or KKKKKWKKWKKK-PSSKSTEIKWKSGKDLTKRSSQ (SEQ ID NO:17, designated as "Mut7DPT-SET2h-S3").

In another embodiment, the pro-apoptotic peptide inhibits binding between SET protein and Caspase-9 protein, as described in international patent application WO2016/156538. More particularly, the pro-apoptotic peptide may comprise or consist of sequence QX$_a$PGCFNFLRKKX$_b$FFKTX$_c$ (SEQ ID NO:18), wherein X$_a$ is methionine or isoleucine, X$_b$ is leucine or phenylananine, X$_c$ is serine or vacant; wherein the pro-apoptotic peptide preferably comprises or consists of QMPGCFNFLRKKLFFKTS (SEQ ID NO:19, designated as "C9h-S4");

ILKVEQKYNKLRQPFFQKRSEL (SEQ ID NO:20, designated as "SET2h-S1");

RSSQTQNKASRKRQHEEP (SEQ ID NO:21, designated as "SET2h-S2");

or a proteolysis-resistant peptide deriving from said pro-apoptotic peptide by one or more chemical modifications, or a substantially homologous peptide, preferably deriving from SEQ ID NO: 18-21 by one or more conservative substitutions.

In another particular embodiment, the pro-apoptotic peptide may comprise, or consist of, a sequence that derives from the binding site of caspase-9 to PP2A, as described in international patent applications WO2010/112471 and WO2013/098337. More particularly the pro-apoptotic peptide comprises or consists of sequence Y-X$_{4a}$-ETLD-X$_{4b}$-I-X$_5$-EQWA-X$_6$-S-X$_7$ (SEQ ID NO: 34)

wherein
X$_{4a}$ is valine or isoleucine;
X$_{4b}$ is aspartic acid or glycine;
X$_5$ is phenylalanine or leucine;
X$_6$ is arginine or histidine;
X$_7$ is vacant or is glutamate, or glutamate-aspartate, or glutamate-aspartate-leucine; preferably wherein X$_{4a}$ is valine; X$_{4b}$ is aspartic acid; X$_5$ is phenylalanine; and X$_6$ is histidine; still preferably wherein the pro-apoptotic peptide comprises or consists of YVETLDDIFEQWAHSEDL (SEQ ID NO: 35, also designated as "C9h-S3") or YIETLDDILEQWARSEDL (SEQ ID NO:36, also designated as "C9m-S3");

or a proteolysis-resistant peptide deriving from said pro-apoptotic peptide by one or more chemical modifications, or a substantially homologous peptide, preferably deriving from SEQ ID NO: 35 or 36 by one or more conservative substitutions.

In an embodiment, the chimeric polypeptide comprises or consists of KKKKKWKKWKKK-YVETLDDIFEQWAHSEDL (SEQ ID NO:37, designated as "Mut7DPT-C9h").

In another embodiment, the pro-apoptotic peptide inhibits the interaction between the TEAD and YAP or TAZ proteins, as described in international patent application WO2015/063747.

More particularly, the pro-apoptotic peptide may comprise or consist of sequence
a) RLQLVEFSAFVEPPDAVD, (SEQ ID NO: 38, designated as "TEAD2h-S1");
b) KTANVPQTVPMRLRKLPD, (SEQ ID NO: 39, designated as "YAP1h-S2");
c) PPHAFFLVKFWADLNWGPSGEEAGAG (SEQ ID NO:40, designated as "TEAD2h-S2");
d) or an amino acid sequence deriving from a sequence in a), b) or c) by a N- and/or C-terminal deletion of 1 to 4 amino acids;
e) a proteolysis-resistant peptide deriving from said pro-apoptotic peptide by one or more chemical modifications, or
f) a substantially homologous peptide, preferably deriving from SEQ ID NO: 38, 39, or 40 by one or more conservative substitutions.

In another embodiment, the pro-apoptotic peptide is a fragment of Ras or Raf protein, or derives therefrom, and binds to Raf or Ras protein, respectively, as described in international patent application WO2015/001045.

More particularly, the pro-apoptotic peptide may comprise or consist of sequence
a) MEHIQGAWKTISNGFGLK (SEQ ID NO:41, designated as "Raf1m-S1");
b) MEHIQGAWKTISNGFGFK (SEQ ID NO:42, designated as "Raf1h-S1");
c) HEHKGKKARLDWNTX$_8$ (SEQ ID NO:43), wherein X$_8$ is absent, is D or is an amino acid sequence selected from the group consisting of DA, DAA, or DAAS, wherein the pro-apoptotic peptide preferably comprises or consists of HEHKGKKARLDWNTDAAS (SEQ ID NO:44, designated as "Raf1h-S2"); or
d) KMSKDGKKKKKKSX$_9$TX$_{10}$CX$_{11}$ (SEQ ID NO:45), wherein X$_9$ and X$_{10}$ are each independently R or K, X$_{11}$ is absent or is one to three amino acids; wherein the pro-apoptotic peptide preferably comprises or consists of sequence KMSKDGKKKKKKSRTRCTVM (SEQ ID NO:46) or KMSKDGKKKKKKSKTKCVIM (SEQ ID NO:47, designated as "KRash-S1");
e) a proteolysis-resistant peptide deriving from said pro-apoptotic peptide by one or more chemical modifications, or
f) a substantially homologous peptide, preferably deriving from SEQ ID NO: 41 to 47 by one or more conservative substitutions.

Peptide Preparation

The (poly)peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloyycarbonyl), Bzl (benzyl), Fmoc (9-fluorenylmcthoxycarbonyl), Mbh (4, 4'-dimethoxydibenzhydryl), Mtr (4-methoxy-2, 3, 6-trimethylbenzenesulphonyl), Trt (trityl), Tos (tosyl), Z (benzyloxycarbonyl) and Clz-Bzl (2, 6-dichlorobenzyl) for the amino groups; NO2 (nitro) and Pmc (2,2, 5,7, 8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid and/or a genetic construct comprising or consisting of a nucleotidic sequence encoding a peptide according to the invention, polynucleotides with nucleotidic sequences complementary to one of the above sequences and sequences hybridizing to said polynucleotides under stringent conditions.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

Thus, in another aspect, it is provided a host or host cell that expresses (or that under suitable circumstances is capable of expressing) a peptide; and/or that contains a polynucleotide or genetic construct as described herein.

The method of producing the peptide may optionally comprise the steps of purifying said peptide, chemically modifying said peptide, and/or formulating said peptide into a pharmaceutical composition.

Further Protection Against Proteolysis

The N- and C-termini of the (poly)peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH-peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

For instance the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides may be composed of amino acid(s) in D configuration, which render the peptides resistant to proteolysis. They may also be stabilized by intramolecular cross-linking, e.g. by modifying at least two amino acid residues with olefinic side chains, preferably C3-C8 alkenyl chains, preferably penten-2-yl chains) followed by chemical cross-linking of the chains, according to the so-called "staple" technology described in Walensky et al, 2004. For instance, amino acids at position i and i+4 to i+7 can be substituted by non-natural aminoacids that show reactive olefinic residues. All these proteolysis-resistant chemically-modified peptides are encompassed in the present invention.

In another aspect, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

Nucleic Acids

The invention also relates to a polynucleotide comprising or consisting of a nucleotide sequence encoding a (poly) peptide according to the invention.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

The genetic constructs may be DNA or RNA, preferably cDNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

In a particular embodiment, the nucleic acid encoding the cell-penetrating peptide of the invention is coupled or fused to a nucleic acid that encodes a peptide or protein of interest. The peptide of interest may be a pro-apoptotic peptide as described herein. More generally it may the peptide or protein of interest may be any peptide or protein to express, such as therapeutic peptide or polypeptide, as well as any antigenic or immunogenic peptide if desired.

The nucleic acid may especially be carried by a viral vector, such as an adenovirus or a lentivirus, for ex vivo or in vivo infection and expression of the chimeric (poly) peptide construct.

Pharmaceutical Compositions

The peptides of the invention (or nucleic acid that encodes said peptide) may be administered by any convenient route including intravenous, oral, transdermal, subcutaneous, mucosal, intramuscular, intrapulmonary, intranasal, parenteral, rectal, vaginal and topical. Intranasal route is of particular interest.

The peptides (or nucleic acid that encodes said peptide) may be typically formulated in association with a pharmaceutically acceptable vehicle.

The pharmaceutical composition may also include any other active principle, such as in particular an anti-tumor agent.

If desired, but not necessarily, the peptides (or nucleic acid that encodes said peptide) may be administered by electroporation. Typically, electroporation consists of injecting compounds, preferably via intramuscular or intradermal route, followed by applying a series of electric pulses by means of electrodes connected to a generator.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

Preparation can involve the formulation of the desired molecule with an agent, such as injectable microspheres, bio-erodible particles, polymeric compounds (such as polylactic acid or polyglycolic acid), beads or liposomes that may provide controlled or sustained release of the product. The dosing is selected by the skilled person so that a therapeutic effect is achieved, and depends on the route of administration and the dosage form that is used. Total daily dose of peptides (or nucleic acid that encodes said peptide) administered to a subject in single or divided doses may be in amounts, for example, of from about 0.001 to about 100 mg/kg body weight daily and preferably 0.01 to 10 mg/kg/day. Preferably, a total daily dose is from about 5 to 25 mg/kg/day. A daily dosage of about 5 mg/kg is still preferred. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated. Preferably the peptide construct (or nucleic acid that encodes said peptide) is administered once a day during a period of at least one week, preferably at least two weeks.

Anti-Tumor Therapy

Another aspect of the present invention relates to a peptide, polynucleotide, and/or vector as described herein, for use in treating a hyperproliferative disorder, preferably a tumor or cancer, preferably in a human patient.

The peptides, polynucleotides, and/or vectors as described herein are useful for treating a tumor, in particular a malignant tumor and preventing or treating metastasis.

The peptides as defined herein, or nucleic acids that encode said peptides, are useful in anti-tumor therapy, preferably as adjuvants in combination with an anti-tumor agent, preferably a chemotherapeutic agent.

Advantageously, intra-tumoral administration is also contemplated.

The anti-tumor therapy of the invention is helpful in eradicating any persistent microscopic malignancy, and/or preventing or delaying relapses.

Furthermore, the peptides (or nucleic acids that encode said peptides) may be used for preventing or treating metastases.

It is thus described a method of treatment of a hyperproliferative disorder, preferably a tumor or cancer, in a patient in need thereof, which method comprises administering said patient with a (poly)peptide of the invention, comprising a pro-apoptotic peptide and a novel CPP.

The tumor may be cancer, such as a haematologic cancer, in particular acute myelogenous leukaemia (AML), chronic lymphocytic leukaemia (CLL), multiple myeloma, Hodgkin's disease, non-Hodgkin's lymphoma, B cell, cutaneous T cell lymphoma, or a non-haematologic cancer, for instance brain, epidermoid (in particular lung, breast, ovarian), head and neck (squamous cell), bladder, gastric, pancreatic, head, neck, renal, prostate, colorectal, oesophageal or thyroid cancer, and melanoma. In a preferred embodiment the peptides described herein (or nucleic acids that encode said peptides) are useful for treatment of chronic lymphocytic leukaemia (CLL).

Different types of cancers may include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendothelio-sarcoma, synovioma, mesothelioma, Ewing's tumor, leiomyosarcoma, rhabdomyosarcoma, lymphoma, leukemia, B-cell chronic lymphocytic leukemia (CLL), B-cell non-Hodgkin lymphoma (NHL), squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma, uveal melanoma and breast cancer.

Further aspects and advantages of the present invention will be disclosed in the following experimental section, which should be regarded as illustrative and not limiting the scope of the present application.

EXAMPLES

Example 1: Design of the Cell Penetrating Peptides (CPPs)

Materials and Methods
Cells and Culture

Breast cancer cell line MCF-7 was cultured in DMEM-Glutamax medium supplemented with 10% of FCS. Jurkat cell line was cultured in RPMI supplemented with 10% FCS. Cells were maintained at 37° C. with 5% of $CO_2$.

Peptide Synthesis

Cell penetrating peptides were synthesized using an automated multiple peptide synthesizer with solid phase procedure and standard Fmoc chemistry. The purity and composition of the peptides were confirmed by reversed phase HPLC and by amino acid analysis. For peptide sequences, see Table 4. All the peptides were labelled with FITC in order to follow the intensity into the cell.

TABLE 4

Shuttle peptides

| Peptide name | SEQ ID NO: | Sequence | Size (aa) | Mw |
|---|---|---|---|---|
| Mut3DPT | 22 | VKKKKIKAEIKI | 12 | 1425.86 |
| Mut4DPT | 4 | VKKWKIKWWIKI | 12 | 1656.14 |
| Mut7DPT | 7 | KKKKKWKKWKKK | 12 | 1672.18 |
| Mut5DPT | 5 | KKWKKWKKWKK | 11 | 1602.05 |
| Mut6DPT | 6 | RRWRRWRRWRR | 11 | 1826.15 |
| Tat 48-60 | 23 | GRKKRRQRRRPPQ | 13 | 1719.04 |
| Penetratin | 24 | RQIKIWFQNRRMKWK | 15 | 2118.54 |
| R8 | 25 | RRRRRRRR | 8 | 1267.52 |

Analysis of Peptide Stability in Human Serum

Mut3DPT, as well as Mut4DPT, Mut5DPT, Mut6DPT and Mut7DPT were incubated at 37° C. in 250 µl human serum for different periods of time. Samples were collected and peptide degradation stopped by freezing. Peptides were extracted from collected samples using the ProteoMiner Protein Enrichment System (Bio-Rad). Peptide integrity (percentage of intact peptide) was analyzed by mass spectrometry using a MALDI-TOF (Brücker Autoflex II) following their standard protocols. Every measurement was performed by triplicate. MS data were analyzed using appropriate software (Clinprot tools, Flex analysis, Brücker).

Intracellular Detection of Peptides by FACS

Jurkat and MCF-7 cells were incubated with different concentrations of FITC-labeled peptides, then washed and analyzed by FACS in order to detect the intensity of fluorescence into the cells. Similarly, Jurkat and MCF-7 cells were incubated with a given peptide concentration at different times and after washing, cells were analyzed by FACS to estimate the intensity of fluorescence into the cells.

Results

Design of the CPPs

The inventors incubated the cells (Jurkat and MCF-7) with the peptides at different concentrations and different times and analyzed the intensity of the fluorescence into the cells by FACS. The result of kinetic of time incubation is shown on FIG. 1 and the kinetic of peptide concentration is shown on FIG. 2.

Regarding the kinetic of incorporation of peptide into the cell, the inventors observed that the peptide Mut6DPT is rapidly internalized. Around 50% of the total fluorescence is achieved as soon as one minute after incubation of cells with the peptide, reaching a plateau upon 15 min.

For peptide Mut7DPT, the inventors observed a plateau upon 30 minutes of incubation. The rest of peptides, Mut4DPT and Mut5DPT, show a better internalization that the control peptide Mut3DPT. All the peptides were tested at 50 µM concentration.

FIG. 2 shows the peptide concentration effect upon fixed incubation time of 4 h. The inventors observed that all the new generated peptides are better internalized than the control peptide Mut3DPT upon 4 hours of incubation.

Finally, FIG. 3 shows that the peptides are not toxic at a high concentration such as 100 µM.

Analyse of the Stability of the New Generated Enhanced Penetration Peptides

The inventors have analyzed whether these new generated peptides have enhanced stability in plasma, compared to the control Mut3DPT. The peptides were incubated for different periods of time (from 0 to 24 h) at 37° C. with human plasma and their stability was analyzed by mass spectrometry (MS). FIG. 4 shows the stability of the peptides compared to the control peptide Mut3DPT. We can observe that the peptide Mut4DPT, generated from Mut3DPT, is as stable as the parental peptide. The synthetic peptides Mut5DPT, Mut6DPT and Mut7DPT are also very stable to proteases degradation, compared to the control peptide Mut3DPT. Taken together, we can conclude that there is no modification of the stability upon 24 h of incubation with human serum.

The stability of the Mut3DPT shuttle was also compared to the well known Tat (48-60), penetratin and R8 shuttles. FIG. 5 shows that upon 6 h of incubation with human serum at 37° C., the three peptides show stronger degradation that the control Mut3DPT peptide, especially Tat and R8 shuttles. All of them are extensively degraded upon 24 h of incubation with human serum.

Taken together, these results suggest that the new generated peptides are stable to proteases degradation and penetrate better and more quickly that the control peptide Mut3DPT in the cell, reducing the time of exposition and the dose needed for a biological effect, as well as the toxicity.

Example 2: Confirmation of the Properties of the CPPs

Materials and Methods
Isolation of Peripheral Blood Mononuclear Cells (PBMC)

Fresh blood samples from healthy donors or chronic lymphocytic leukaemia (CLL) patients were obtained from EFS and haematology department, respectively. PBMC were isolated by Ficoll gradient centrifugation. B cells were selected with anti hCD19-APC labelled antibody.

Detection of Apoptosis by Annexin Staining

The apoptosis induction of the different shuttles associated to a cargo (PP2A/SET binding site) was analyzed by annexinV-FITC staining (e Biosciences). Human breast cancer cell line MCF7 and human T cell line Jurkat were treated with different concentrations of peptide for 24 h. After the treatment, cells were harvested, washed and treated according to the manufacture-s protocol. The level of apoptosis was measured by flow cytometry (BD Biosciences, FACS Canto). B cells from healthy donor or CLL patients were stained with anti-hCD19-APC labelled antibody (BD Biosciences) after annexin staining.

Quantification of Cellular Internalization

Peripheral blood mononuclear cells from healthy (HD) donors or chronic lymphocytic leukaemia patients (CLL) were treated with FITC-labelled peptides and them, cells were harvested and washed twice with PBS to remove the extracellular unbound peptide. FITC fluorescence intensity of internalized peptide was measured by flow cytometry (BD Biosciences) by acquiring 10,000 live cells. B cells were selected with anti hCD19-APC labelled antibody. Experiments were carried out three times in duplicate. Untreated cells were used as control.

Peptides Internalization Visualization

For intracellular localization of FITC-labelled peptides, MDA-MB231 or MCF7 cells were seeded in an 8-well Labtek (Thermo Fischer) at a density of $2 \times 10^4$ cells/well. Cells were treated with different concentrations of FITC-labelled peptides for different times. Cells were fixed with 4% of formaldehyde for 15 min at room temperature. Samples were washed twice with PBS and mounted in mounting solution containing DAPI. Images were captured with a fluorescence microscopy (Olympus Japan) using 63× magnification objective.

Analysis of Peptide Stability in Serum

Peptides were incubated at 37° C. in 250 μl of human serum for different periods of time. Samples were collected and peptides degradation stopped by freezing. Peptides were extracted from samples using the Proteo Miner Protein Enrichment System (Bio-Rad). Peptide integrity (percentage of intact peptide) was analyzed by mass spectrometry (MS) using MALDI-TOF (Brucker Autoflex II) following their standard protocols. Measurements were performed in triplicate. MS data were analyzed using appropriate software (Clinprot tools, Flex analysis, Brucker).

Intracellular Detection of Peptides by Mass Spectrometry (MS)

To detect the internalization of the peptides, breast cancer cell line MCF-7 cells were seeded in a 6-well plate at a density of $1 \times 10^6$ cells/well in DMEM medium supplemented with 10% FCS. Cells were treated with 100 μM of each shuttle for 4 h at 37° C., then cells were washed once with PBS. Cell pellet was collected by detaching with Trypsin EDTA following several washing step with PBS. Cells were resuspended in lysis buffer (Tris-HCl 50 mM, NaCl 20 mM, pH 8.0, supplemented with protease inhibitors) and lysed with Glass/Teflon potter (Elvehjem homogenizers), then centrifuged for 20 min at 16,000 g at 4° C. The peptides in the supernatant were concentrated with Ziptips (Millpore, ZTC18S096) according to the manufacture's protocol. The internalization of peptide was detected by mass spectrometry (MS) using a MALDI-TOF (Brucker Autoflx II). MS data were analyzed using appropriate software (Clinprot tools, Flex analysis, Brucker).

TABLE 5

Characteristics of the shuttles associated to a cargo

| Peptide name | SEQ ID NO: | Sequence | Size (aa) | Mw |
|---|---|---|---|---|
| Mut3DPT-PP2A/SET | 48 | VKKKKIKAEIKIETVTLLVALKVRYRERIT | 30 | 3568.91 |
| Mut4DPT-PP2A/SET | 49 | VKKWKIKWWIKIETVTLLVALKVRYRERIT | 30 | 3799.19 |
| Mut5DPT-PP2A/SET | 50 | KKWKKWKKWKKETVTLLVALKVRYRERIT | 29 | 3745.07 |
| Mut6DPT-PP2A/SET | 14 | RRWRRWRRWRRETVTLLVALKVRYRERIT | 29 | 3969.15 |
| Mut7DPT-PP2A/SET | 16 | KKKKKWKKWKKKETVTLLVALKVRYRERIT | 30 | 3815.22 |

Results

The inventors incubated the cells (MCF-7, PBMC) with the peptides at different concentrations (respectively 25 μM, and 100 μM) and analyzed the presence of the shuttles into the cells by fluorescence microscopy, mass spectrometry (MS) and flow cytometry. FIG. 6 shows the intracellular localization of FITC-labelled shuttles by fluorescence microscopy. FIG. 7 shows the intracellular detection by mass spectrometry (MS) of the shuttles. FIG. 8 shows the internalization of FITC-labelled shuttles on healthy and tumoral primary B cells, by flow cytometry.

These results confirm the better internalization of peptides Mut4DPT, Mut5DPT, Mut6DPT and Mut7DPT compared to the control peptide Mut3DPT, with a better internalization for peptides Mut6DPT and Mut7DPT.

Analyse of the Stability of the New Generated Enhanced Penetration Peptides Associated to a Cargo (PP2AISET Binding Site)

The inventors have analyzed whether these new generated peptides associated to a cargo (PP2A/SET binding site) have enhanced stability in plasma, compared to the control Mut3DPT. The peptides were incubated for different periods of time (from 0 to 24 h) at 37° C. with human plasma and their stability was analyzed by mass spectrometry (MS). FIG. 9 shows the stability in human serum of the shuttles associated to a cargo (PP2A/SET binding site).

Analyse of the Apoptosis Induced by the New Generated Enhanced Penetration Peptides Associated to a Pro-Apoptotic Peptide (PP2AISET Binding Site)

The inventors have analyzed whether these new generated peptides associated to a pro-apoptotic peptide (PP2A/SET binding site) have enhanced pro-apoptotic activity, compared to the control Mut3DPT associated to the pro-apoptotic peptide (PP2A/SET binding site). MCF-7 cells were incubated with the peptides associated to the cargo (PP2A/SET binding site) at different concentrations (10, 25, 50 and 100 μM) during 24 hours and the apoptosis was analyzed by Annexin-V-FITC staining. Non treated cells were used as control. FIG. 10 shows the detection of apoptosis induced by the shuttle associated to the cargo.

The results shows that the new generated peptides associated to a pro-apoptotic peptide (PP2A/SET binding site) possess an enhanced pro-apoptotic activity compared to the control peptide Mut3DPT associated to the same pro-apoptotic peptide (PP2A/SET binding site).

Example 3: Peptides Designed for Nuclear Localisation

Materials and Methods
Peptide Synthesis

Peptides were synthesized in an automated multiple peptide synthesizer with solid phase procedure and standard Fmoc chemistry. The purity and composition of the peptides were confirmed by reverse phase HPLC and by mass spectrometry (MS). The peptides were also synthesized whit a fluorochrome (FITC) in C-terminal.

TABLE 6

The peptides designed

| Peptide name | SEQ ID NO: | Sequence |
|---|---|---|
| NLS18 | 27 | RKR-KKKKKWKKW-PKKKKLD |
| NLS23 | 28 | RKR-KKKKKWKKWKKK-PKKKKLD |
| NLS18-YAP | 31 | RKR-KKKKKWKKW-PKKKKLD-KTANVPQTVPMRLRKLPD |
| NLS18-TEAD | 29 | RKR-KKKKKWKKW-PKKKKLD-RLQLVEFSAFVEPPDAVD |
| NLS23-YAP | 32 | RKR-KKKKKWKKWKKK-PKKKKLD-KTANVPQTVPMRLRKLPD |
| NLS23-TEAD | 30 | RKR-KKKKKWKKWKKK-PKKKKLD-RLQLVEFSAFVEPPDAVD |
| mut3DPT-TEAD | 51 | VKKKKIKAEIKI-RLQLVEFSAFVEPPDAVD |

Cell Culture

Breast cancer cell line MDA-MB231 were cultured in DMEM supplemented with 10% of foetal calf serum (FCS).
Quantification of Cellular Internalization Human breast cancer cell line MDA-MB231 was seeded in 24 well plates (5×105 cells/well). Cells were treated with different concentrations of FITC-labelled peptides for different periods of time. After the treatment with FITC-labelled shuttles, cells were harvested and washed twice with PBS to remove the extracellular unbound peptide. Cells were treated with trypsin for 5 min to remove non-internalized surface bound peptide and then, centrifuged, washed and resuspended in 200 µl of PBS. FITC fluorescence intensity of internalized peptide was measured by flow cytometry (BD Biosciences) by acquiring 10,000 live cells. Experiments were carried out three times in duplicate. Untreated cells were used as control.
Detection of Apoptosis by Annexin Staining The apoptosis induction of the different shuttles associated to a cargo (TEAD and YAP binding sites) was analyzed by annexinV-FITC staining (e Biosciences). Human breast cancer cell line MDA-MB231 was treated with different concentrations of peptide for 4 h and 24 h. After the treatment, cells were harvested, washed and treated according to the manufacturer protocol. The level of apoptosis was measured by flow cytometry (BD Biosciences, FACS Canto.
Peptides Internalization Visualization For intracellular localization of FITC-labelled peptides, MDA-MB231 was seeded in an 8-well Labtek (Thermo Fischer) at a density of 3×104 cells/well. Cells were treated with different concentrations of FITC-labelled peptides for different times. Cells were fixed or not with 4% of formaldehyde for 15 min at room temperature. Samples were washed twice with PBS and mounted in mounting solution containing DAPI. Images were captured with a fluorescence microscopy (Olympus Japan) using 63× magnification objective.

Results
Analysis of the Toxicity of the CPP-NLS Peptides

We analyzed the toxicity of RKR-KKKKKWKKW-PKKKKLD (SEQ ID NO:27, NLS18), RKR-KKKKKWKKWKKK-PKKKKLD (SEQ ID NO: 28, NLS23) and the control KKKKKWKKWKKK mut7DPT (SEQ ID NO: 7 which is a CPP without NLS sequence). The peptides were added to MDA-MB231 cell line at 25 and 50 µM and the toxicity was analyzed by FACS upon 4 h of incubation. As shown on FIG. 11, none of the peptides show toxicity, independently of the concentration used.
Quantification of Internalization of Peptides We evaluated whether peptides NLS18 and NLS23 which include a nuclear localisation signal (NLS) were able to internalize into cells. The peptides were labelled with FITC and their internalization was analyzed by flow cytometry (FACS). mut7DPT, the CPP without NLS was used as a control. MDA-MB231 cells were treated with FITC-labelled peptides at different concentrations for 4 h and then, internalization was analyzed by FACS. FIG. 12 shows the internalization of the NLS18 and NLS23 compared to mut7DPT control peptide. Both peptides show higher internalization than the control peptide. Between the two peptides, NLS18 shows better internalization than NLS23 (FIG. 12). Taken together, the new generated peptide constructs show a better internalization profile than the control mut7DPT.
Intracellular Localization of NLS18 and NLS23

To confirm the FACS results and to visualize the intracellular distribution of NLS18 and NLS23 we stained MDA-MB231 cells with FITC-labelled peptides and analyzed the penetration by fluorescence microscopy following 4 h of incubation at a concentration of 30 µM (FIG. 13). We observed a punctuate nuclear staining for NLS18 and NLS23 with low cytoplasmic staining. The control mut7DPT-FITC peptide does not show nuclear staining, confirming the results of FACS.

We further analyzed the effect of time incubation in the internalization on a fixed peptide concentration (30 µM). Among them, NLS23 showed rapid internalization, being in the nucleus upon 15 min of incubation with the cells. NLS18 is detected in the nucleus upon 30 min of incubation (FIG. 14). Taken together, NLS18 and NLS23 show more favourable internalization than the control, with a specific nuclear localization.
Impact of a Cargo on the Properties of NLS18 and NLS23

We first analyzed the impact on the nuclear localization of the association of the interfering peptides blocking the interaction between TEAD (RLQLVEFSAFVEPPDAVD, SEQ ID NO: 38) and YAP (KTANVPQTVPMRLRKLPD, SEQ ID NO: 39). The new generated tri-functional peptides labelled with FITC were incubated with MDA-MB231 cells for 3 h with 15 µM of the new peptides. FIG. 15 shows that the association of a cargo to NLS18 or NLS23 does not affect the nuclear localization of NLS18 and NLS23.

We further analyzed whether the weak apoptotic effect of the mut3DPT-TEAD peptide was increased in the new generated tri-functional peptides. Cells were cultured for 4 h or 24 h with 10 and 25 µM of NLS-18 or NLS-23 and apoptosis estimated by Annexin staining (FIG. 16). The association of TEAD interfering peptide to the NLS18 or NLS23 peptides strongly increases the apoptotic effect, compared to the control peptide.

Taken together, these results show that we have generated new CPPs with nuclear localization that are able to transport a cargo to the nucleus.

The invention claimed is:

1. A chimeric construct comprising a cargo molecule linked to a cell penetrating moiety consisting of SEQ ID NO: 7 or SEQ ID NO: 9.

2. The chimeric construct of claim 1, wherein the cell penetrating moiety consists of SEQ ID NO: 7 or SEQ ID NO: 9 and the cargo molecule is selected from the group consisting of a peptide, a protein, a nucleic acid, and a small molecule.

3. The chimeric construct of claim 2, wherein said construct is a chimeric polypeptide comprising said cell penetrating moiety and a peptide as the cargo molecule, said chimeric polypeptide consisting of no more than 100 amino acids.

4. The chimeric construct of claim 1, wherein the cell penetrating moiety is fused to at least one nuclear localization amino acid sequence.

5. The chimeric construct of claim 4, wherein the nuclear localization amino acid sequence is bipartite and comprises a) RKR fused at N-terminus of the cell penetrating moiety sequence and b) SEQ ID NO: 26 fused at C-terminus of the cell penetrating moiety sequence.

6. The chimeric construct of claim 1, wherein the cargo molecule is therapeutic agent.

7. The chimeric construct of claim 1, wherein the cargo molecule is labelling agent.

8. The chimeric construct of claim 1, said construct being a chimeric polypeptide comprising a pro-apoptotic peptide as the cargo molecule.

9. The chimeric construct of claim 1, which is a chimeric polypeptide comprising i) SEQ ID NO: 27 or SEQ ID NO: 28 fused to ii) a pro-apoptotic peptide as the cargo molecule.

10. The chimeric construct of claim 1, wherein the cargo molecule is a pro-apoptotic peptide comprising:
    a) RLQLVEFSAFVEPPDAVD, (SEQ ID NO: 38, designated as "TEAD2h-S1");
    b) KTANVPQTVPMRLRKLPD, (SEQ ID NO: 39, designated as "YAP1h-S2");
    c) PPHAFFLVKFWADLNWGPSGEEAGAG (SEQ ID NO: 40, designated as "TEAD2h-S2");
    d) or an amino acid sequence derived from a), b) or c) by a N- and/or C-terminal deletion of 1 to 4 amino acids; or
    e) a proteolysis-resistant peptide of said pro-apoptotic peptide comprising one or more chemical modifications.

11. The chimeric construct of claim 1, wherein the cargo molecule is a pro-apoptotic peptide comprising RLQLVEFSAFVEPPDAVD (SEQ ID NO: 38) or KTANVPQTVPMRLRKLPD (SEQ ID NO: 39).

12. The chimeric construct of claim 1, which is a chimeric polypeptide that comprises or consists of a sequence selected from the group consisting of:

```
                                          (SEQ ID NO: 29)
RKR-KKKKKWKKW-PKKKKLD-RLQLVEFSAFVEPPDAVD;

(SEQ ID NO: 30)
RKR-KKKKKWKKWKKK-PKKKKLD-RLQLVEFSAFVEPPDAVD;

(SEQ ID NO: 31)
RKR-KKKKKWKKW-PKKKKLD-KTANVPQTVPMRLRKLPD;
and (SEQ ID NO: 32)
RKR-KKKKKWKKWKKK-PKKKKLD-KTANVPQTVPMRLRKLPD.
```

13. The chimeric construct of claim 1, wherein the cargo molecule is a pro-apoptotic peptide comprising or consisting of ETVTLLVALKVRYRERIT (SEQ ID NO: 12) or PSSKSTEIKWKSGKDLTKRSSQ (SEQ ID NO:13), or a proteolysis-resistant peptide deriving from said pro-apoptotic peptide by one or more chemical modifications.

14. A chimeric (poly)peptide comprising a peptide or a protein and a sequence selected from the group consisting of KKKKKWKKWKKK (SEQ ID NO: 7); KKKKKWKKW (SEQ ID NO: 9); RKR-KKKKKWKKW-PKKKKLD (SEQ ID NO: 27); and RKR-KKKKKWKKWKKK-PKKKKLD (SEQ ID NO: 28).

15. A method of imaging comprising contacting a cell with a chimeric construct according to claim 7 and imaging said cell.

* * * * *

UNITED STATES PATENT AND TRADEMARK OFFICE
CERTIFICATE OF CORRECTION

PATENT NO. : 10,947,276 B2
APPLICATION NO. : 16/472226
DATED : March 16, 2021
INVENTOR(S) : Angelita Rebollo et al.

Page 1 of 1

It is certified that error appears in the above-identified patent and that said Letters Patent is hereby corrected as shown below:

In the Specification

Column 4,
Line 42, "a helix" should read --α helix--.

Column 6,
Line 59, "hydrophilio-basic" should read --hydrophilic-basic--.

Column 18,
Line 38, "(PP2AISET" should read --(PP2A/SET--.
Line 50, "(PP2AISET" should read --(PP2A/SET--.

Signed and Sealed this
Ninth Day of November, 2021

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 51

<210> SEQ ID NO 1
<211> LENGTH: 8
<212> TYPE: PRT
<213> ORGANISM: Artificial Sequence
<220> FEATURE:
<223> OTHER INFORMATION: shuttle peptide of Formula (I)
<220> FEATURE:
<221> NAME/KEY: MISC_FEATURE
<222> LOCATION: (1)..(1)
<223> OTHER INFORMATION: Xaa at position 1 is KK or RR
<220> FEATURE:
<221> NAME/KEY: MISC_FEATURE
<222> LOCATION: (2)..(2)
<223> OTHER INFORMATION: Xaa at position 2 is K or W
<220> FEATURE:
<221> NAME/KEY: MISC_FEATURE
<222> LOCATION: (3)..(3)
<223> OTHER INFORMATION: Xaa at position 3 is KK or RR
<220> FEATURE:
<221> NAME/KEY: MISC_FEATURE
<222> LOCATION: (5)..(5)
<223> OTHER INFORMATION: Xaa at position 5 is KK or RR
<220> FEATURE:
<221> NAME/KEY: MISC_FEATURE
<222> LOCATION: (7)..(7)
<223> OTHER INFORMATION: Xaa at position 7 is KK or RR
<220> FEATURE:
<221> NAME/KEY: MISC_FEATURE
<222> LOCATION: (8)..(8)
<223> OTHER INFORMATION: Xaa at position 8 is K or W
<220> FEATURE:
<221> NAME/KEY: MISC_FEATURE
<222> LOCATION: (8)..(8)
<223> OTHER INFORMATION: Xaa at position 8 is K or vacant

<400> SEQUENCE: 1

Xaa Xaa Xaa Trp Xaa Trp Xaa Xaa
1               5

<210> SEQ ID NO 2
<211> LENGTH: 6
<212> TYPE: PRT
<213> ORGANISM: Artificial Sequence
<220> FEATURE:
<223> OTHER INFORMATION: Shuttle peptide of formula (II)
<220> FEATURE:
<221> NAME/KEY: MISC_FEATURE
<222> LOCATION: (1)..(1)
<223> OTHER INFORMATION: Xaa at position 1 is KK or RR
<220> FEATURE:
<221> NAME/KEY: MISC_FEATURE
<222> LOCATION: (2)..(2)
<223> OTHER INFORMATION: Xaa at position 1 is K or W
<220> FEATURE:
<221> NAME/KEY: MISC_FEATURE
<222> LOCATION: (3)..(3)
<223> OTHER INFORMATION: Xaa at position 3 is KK or RR
<220> FEATURE:
<221> NAME/KEY: MISC_FEATURE
<222> LOCATION: (5)..(5)
<223> OTHER INFORMATION: Xaa at position 5 is KK or RR

<400> SEQUENCE: 2

Xaa Xaa Xaa Trp Xaa Trp
1               5

<210> SEQ ID NO 3
<211> LENGTH: 10
<212> TYPE: PRT
<213> ORGANISM: Artificial Sequence
<220> FEATURE:
<223> OTHER INFORMATION: Shuttle peptide of formula (III)

```
<220> FEATURE:
<221> NAME/KEY: MISC_FEATURE
<222> LOCATION: (1)..(1)
<223> OTHER INFORMATION: Xaa at position 1 is V or vacant
<220> FEATURE:
<221> NAME/KEY: MISC_FEATURE
<222> LOCATION: (10)..(10)
<223> OTHER INFORMATION: Xaa at position 10 is IKI or vacant

<400> SEQUENCE: 3

Xaa Lys Lys Trp Lys Ile Lys Trp Trp Xaa
1               5                   10

<210> SEQ ID NO 4
<211> LENGTH: 12
<212> TYPE: PRT
<213> ORGANISM: Artificial Sequence
<220> FEATURE:
<223> OTHER INFORMATION: shuttle peptide Mut4DPT

<400> SEQUENCE: 4

Val Lys Lys Trp Lys Ile Lys Trp Trp Ile Lys Ile
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Shuttle peptide Mut5DPT

<400> SEQUENCE: 5

Lys Lys Trp Lys Lys Trp Lys Lys Trp Lys Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Shuttle peptide Mut6DPT

<400> SEQUENCE: 6

Arg Arg Trp Arg Arg Trp Arg Arg Trp Arg Arg
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Shuttle peptide Mut7DPT

<400> SEQUENCE: 7

Lys Lys Lys Lys Lys Trp Lys Lys Trp Lys Lys Lys
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Shuttle peptide

<400> SEQUENCE: 8

Arg Arg Trp Arg Arg Trp Arg Arg Trp
1               5
```

<210> SEQ ID NO 9
<211> LENGTH: 9
<212> TYPE: PRT
<213> ORGANISM: Artificial Sequence
<220> FEATURE:
<223> OTHER INFORMATION: Shuttle peptide

<400> SEQUENCE: 9

Lys Lys Lys Lys Lys Trp Lys Lys Trp
1               5

<210> SEQ ID NO 10
<211> LENGTH: 9
<212> TYPE: PRT
<213> ORGANISM: Artificial Sequence
<220> FEATURE:
<223> OTHER INFORMATION: Shuttle peptide

<400> SEQUENCE: 10

Lys Lys Trp Lys Lys Trp Lys Lys Trp
1               5

<210> SEQ ID NO 11
<211> LENGTH: 9
<212> TYPE: PRT
<213> ORGANISM: Artificial Sequence
<220> FEATURE:
<223> OTHER INFORMATION: Shuttle peptide

<400> SEQUENCE: 11

Val Lys Lys Trp Lys Ile Lys Trp Trp
1               5

<210> SEQ ID NO 12
<211> LENGTH: 18
<212> TYPE: PRT
<213> ORGANISM: Artificial Sequence
<220> FEATURE:
<223> OTHER INFORMATION: proapoptotic peptide PP2Ach-S2

<400> SEQUENCE: 12

Glu Thr Val Thr Leu Leu Val Ala Leu Lys Val Arg Tyr Arg Glu Arg
1               5                   10                  15

Ile Thr

<210> SEQ ID NO 13
<211> LENGTH: 22
<212> TYPE: PRT
<213> ORGANISM: Artificial Sequence
<220> FEATURE:
<223> OTHER INFORMATION: proapoptotic peptide SET2h-S3

<400> SEQUENCE: 13

Pro Ser Ser Lys Ser Thr Glu Ile Lys Trp Lys Ser Gly Lys Asp Leu
1               5                   10                  15

Thr Lys Arg Ser Ser Gln
            20

<210> SEQ ID NO 14
<211> LENGTH: 29
<212> TYPE: PRT
<213> ORGANISM: Artificial Sequence
<220> FEATURE:
<223> OTHER INFORMATION: chimeric peptide Mut6DPT-PP2Ach-S2

<400> SEQUENCE: 14

Arg Arg Trp Arg Arg Trp Arg Arg Trp Arg Arg Glu Thr Val Thr Leu
1               5                   10                  15

Leu Val Ala Leu Lys Val Arg Tyr Arg Glu Arg Ile Thr
            20                  25

<210> SEQ ID NO 15
<211> LENGTH: 33
<212> TYPE: PRT
<213> ORGANISM: Artificial Sequence
<220> FEATURE:
<223> OTHER INFORMATION: chimeric peptide Mut6DPT-SET2h-S3

<400> SEQUENCE: 15

Arg Arg Trp Arg Arg Trp Arg Arg Trp Arg Arg Pro Ser Ser Lys Ser
1               5                   10                  15

Thr Glu Ile Lys Trp Lys Ser Gly Lys Asp Leu Thr Lys Arg Ser Ser
            20                  25                  30

Gln

<210> SEQ ID NO 16
<211> LENGTH: 30
<212> TYPE: PRT
<213> ORGANISM: Artificial Sequence
<220> FEATURE:
<223> OTHER INFORMATION: chimeric peptide Mut7DPT-PP2Ach-S2

<400> SEQUENCE: 16

Lys Lys Lys Lys Lys Trp Lys Lys Trp Lys Lys Glu Thr Val Thr
1               5                   10                  15

Leu Leu Val Ala Leu Lys Val Arg Tyr Arg Glu Arg Ile Thr
            20                  25                  30

<210> SEQ ID NO 17
<211> LENGTH: 34
<212> TYPE: PRT
<213> ORGANISM: Artificial Sequence
<220> FEATURE:
<223> OTHER INFORMATION: Chimeric peptide Mut7DPT-SET2h-S3

<400> SEQUENCE: 17

Lys Lys Lys Lys Lys Trp Lys Lys Trp Lys Lys Pro Ser Ser Lys
1               5                   10                  15

Ser Thr Glu Ile Lys Trp Lys Ser Gly Lys Asp Leu Thr Lys Arg Ser
            20                  25                  30

Ser Gln

<210> SEQ ID NO 18
<211> LENGTH: 18
<212> TYPE: PRT
<213> ORGANISM: Artificial Sequence
<220> FEATURE:
<223> OTHER INFORMATION: proapoptotic peptide
<220> FEATURE:
<221> NAME/KEY: MISC_FEATURE
<222> LOCATION: (2)..(2)
<223> OTHER INFORMATION: Xaa at position 2 is M or L
<220> FEATURE:
<221> NAME/KEY: MISC_FEATURE
<222> LOCATION: (13)..(13)
<223> OTHER INFORMATION: Xaa at position 13 is L or F
<220> FEATURE:
<221> NAME/KEY: MISC_FEATURE
<222> LOCATION: (18)..(18)
<223> OTHER INFORMATION: Xaa at position 18 is serine or vacant

```
<400> SEQUENCE: 18

Gln Xaa Pro Gly Cys Phe Asn Phe Leu Arg Lys Lys Xaa Phe Phe Lys
1               5                   10                  15

Thr Xaa

<210> SEQ ID NO 19
<211> LENGTH: 18
<212> TYPE: PRT
<213> ORGANISM: Artificial Sequence
<220> FEATURE:
<223> OTHER INFORMATION: proapoptotic peptide C9h-S4

<400> SEQUENCE: 19

Gln Met Pro Gly Cys Phe Asn Phe Leu Arg Lys Lys Leu Phe Phe Lys
1               5                   10                  15

Thr Ser

<210> SEQ ID NO 20
<211> LENGTH: 22
<212> TYPE: PRT
<213> ORGANISM: Artificial Sequence
<220> FEATURE:
<223> OTHER INFORMATION: proapoptotic peptide SET2h-S1

<400> SEQUENCE: 20

Ile Leu Lys Val Glu Gln Lys Tyr Asn Lys Leu Arg Gln Pro Phe Phe
1               5                   10                  15

Gln Lys Arg Ser Glu Leu
            20

<210> SEQ ID NO 21
<211> LENGTH: 18
<212> TYPE: PRT
<213> ORGANISM: Artificial Sequence
<220> FEATURE:
<223> OTHER INFORMATION: proapoptotic peptide SET2h-S2

<400> SEQUENCE: 21

Arg Ser Ser Gln Thr Gln Asn Lys Ala Ser Arg Lys Arg Gln His Glu
1               5                   10                  15

Glu Pro

<210> SEQ ID NO 22
<211> LENGTH: 12
<212> TYPE: PRT
<213> ORGANISM: Artificial Sequence
<220> FEATURE:
<223> OTHER INFORMATION: shuttle peptide Mut3DPT

<400> SEQUENCE: 22

Val Lys Lys Lys Lys Ile Lys Ala Glu Ile Lys Ile
1               5                   10

<210> SEQ ID NO 23
<211> LENGTH: 13
<212> TYPE: PRT
<213> ORGANISM: Artificial Sequence
<220> FEATURE:
<223> OTHER INFORMATION: shuttle TAT peptide

<400> SEQUENCE: 23

Gly Arg Lys Lys Arg Arg Gln Arg Arg Arg Pro Pro Gln
1               5                   10
```

<210> SEQ ID NO 24
<211> LENGTH: 15
<212> TYPE: PRT
<213> ORGANISM: Artificial Sequence
<220> FEATURE:
<223> OTHER INFORMATION: penetratin

<400> SEQUENCE: 24

Arg Gln Ile Lys Ile Trp Phe Gln Asn Arg Arg Met Lys Trp Lys
1               5                   10                  15

<210> SEQ ID NO 25
<211> LENGTH: 8
<212> TYPE: PRT
<213> ORGANISM: Artificial Sequence
<220> FEATURE:
<223> OTHER INFORMATION: peptide R8

<400> SEQUENCE: 25

Arg Arg Arg Arg Arg Arg Arg Arg
1               5

<210> SEQ ID NO 26
<211> LENGTH: 7
<212> TYPE: PRT
<213> ORGANISM: Artificial Sequence
<220> FEATURE:
<223> OTHER INFORMATION: NLS C-terminus

<400> SEQUENCE: 26

Pro Lys Lys Lys Lys Leu Asp
1               5

<210> SEQ ID NO 27
<211> LENGTH: 19
<212> TYPE: PRT
<213> ORGANISM: Artificial Sequence
<220> FEATURE:
<223> OTHER INFORMATION: NLS18

<400> SEQUENCE: 27

Arg Lys Arg Lys Lys Lys Lys Lys Trp Lys Lys Trp Pro Lys Lys Lys
1               5                   10                  15

Lys Leu Asp

<210> SEQ ID NO 28
<211> LENGTH: 22
<212> TYPE: PRT
<213> ORGANISM: Artificial Sequence
<220> FEATURE:
<223> OTHER INFORMATION: NLS23

<400> SEQUENCE: 28

Arg Lys Arg Lys Lys Lys Lys Lys Trp Lys Lys Trp Lys Lys Lys Pro
1               5                   10                  15

Lys Lys Lys Lys Leu Asp
            20

<210> SEQ ID NO 29
<211> LENGTH: 37
<212> TYPE: PRT
<213> ORGANISM: Artificial Sequence
<220> FEATURE:
<223> OTHER INFORMATION: NLS18-TEAD

<400> SEQUENCE: 29

```
Arg Lys Arg Lys Lys Lys Lys Trp Lys Lys Trp Pro Lys Lys Lys
1               5                   10                  15

Lys Leu Asp Arg Leu Gln Leu Val Glu Phe Ser Ala Phe Val Glu Pro
                20                  25                  30

Pro Asp Ala Val Asp
        35

<210> SEQ ID NO 30
<211> LENGTH: 40
<212> TYPE: PRT
<213> ORGANISM: Artificial Sequence
<220> FEATURE:
<223> OTHER INFORMATION: NLS23-TEAD

<400> SEQUENCE: 30

Arg Lys Arg Lys Lys Lys Lys Trp Lys Lys Trp Lys Lys Lys Pro
1               5                   10                  15

Lys Lys Lys Lys Leu Asp Arg Leu Gln Leu Val Glu Phe Ser Ala Phe
                20                  25                  30

Val Glu Pro Pro Asp Ala Val Asp
        35                  40

<210> SEQ ID NO 31
<211> LENGTH: 37
<212> TYPE: PRT
<213> ORGANISM: Artificial Sequence
<220> FEATURE:
<223> OTHER INFORMATION: NLS18-YAP

<400> SEQUENCE: 31

Arg Lys Arg Lys Lys Lys Lys Trp Lys Lys Trp Pro Lys Lys Lys
1               5                   10                  15

Lys Leu Asp Lys Thr Ala Asn Val Pro Gln Thr Val Pro Met Arg Leu
                20                  25                  30

Arg Lys Leu Pro Asp
        35

<210> SEQ ID NO 32
<211> LENGTH: 40
<212> TYPE: PRT
<213> ORGANISM: Artificial Sequence
<220> FEATURE:
<223> OTHER INFORMATION: NLS23-YAP

<400> SEQUENCE: 32

Arg Lys Arg Lys Lys Lys Lys Trp Lys Lys Trp Lys Lys Lys Pro
1               5                   10                  15

Lys Lys Lys Lys Leu Asp Lys Thr Ala Asn Val Pro Gln Thr Val Pro
                20                  25                  30

Met Arg Leu Arg Lys Leu Pro Asp
        35                  40

<210> SEQ ID NO 33
<211> LENGTH: 18
<212> TYPE: PRT
<213> ORGANISM: Artificial Sequence
<220> FEATURE:
<223> OTHER INFORMATION: PP2A/SET

<400> SEQUENCE: 33

Glu Thr Val Thr Leu Leu Val Ala Leu Lys Val Arg Tyr Arg Glu Arg
1               5                   10                  15
```

Ile Thr

```
<210> SEQ ID NO 34
<211> LENGTH: 16
<212> TYPE: PRT
<213> ORGANISM: Artificial Sequence
<220> FEATURE:
<223> OTHER INFORMATION: Pro-apoptotic peptide
<220> FEATURE:
<221> NAME/KEY: MISC_FEATURE
<222> LOCATION: (2)..(2)
<223> OTHER INFORMATION: Xaa at position 2 is V or I
<220> FEATURE:
<221> NAME/KEY: MISC_FEATURE
<222> LOCATION: (7)..(7)
<223> OTHER INFORMATION: Xaa at position 7 is D or G
<220> FEATURE:
<221> NAME/KEY: MISC_FEATURE
<222> LOCATION: (9)..(9)
<223> OTHER INFORMATION: Xaa at position 9 is F or L
<220> FEATURE:
<221> NAME/KEY: MISC_FEATURE
<222> LOCATION: (14)..(14)
<223> OTHER INFORMATION: Xaa at position 14 is R or H
<220> FEATURE:
<221> NAME/KEY: MISC_FEATURE
<222> LOCATION: (16)..(16)
<223> OTHER INFORMATION: Xaa at position 16 is E or ED or EDL or vacant

<400> SEQUENCE: 34

Tyr Xaa Glu Thr Leu Asp Xaa Ile Xaa Glu Gln Trp Ala Xaa Ser Xaa
1               5                   10                  15

<210> SEQ ID NO 35
<211> LENGTH: 18
<212> TYPE: PRT
<213> ORGANISM: Artificial Sequence
<220> FEATURE:
<223> OTHER INFORMATION: C9h-S3

<400> SEQUENCE: 35

Tyr Val Glu Thr Leu Asp Asp Ile Phe Glu Gln Trp Ala His Ser Glu
1               5                   10                  15

Asp Leu

<210> SEQ ID NO 36
<211> LENGTH: 18
<212> TYPE: PRT
<213> ORGANISM: Artificial Sequence
<220> FEATURE:
<223> OTHER INFORMATION: C9m-S3

<400> SEQUENCE: 36

Tyr Ile Glu Thr Leu Asp Asp Ile Leu Glu Gln Trp Ala Arg Ser Glu
1               5                   10                  15

Asp Leu

<210> SEQ ID NO 37
<211> LENGTH: 30
<212> TYPE: PRT
<213> ORGANISM: Artificial Sequence
<220> FEATURE:
<223> OTHER INFORMATION: Mut7DPT-C9h

<400> SEQUENCE: 37

Lys Lys Lys Lys Lys Trp Lys Lys Trp Lys Lys Lys Tyr Val Glu Thr
1               5                   10                  15
```

-continued

Leu Asp Asp Ile Phe Glu Gln Trp Ala His Ser Glu Asp Leu
            20                  25                  30

<210> SEQ ID NO 38
<211> LENGTH: 18
<212> TYPE: PRT
<213> ORGANISM: Artificial Sequence
<220> FEATURE:
<223> OTHER INFORMATION: TEAD2h-S1

<400> SEQUENCE: 38

Arg Leu Gln Leu Val Glu Phe Ser Ala Phe Val Glu Pro Pro Asp Ala
1               5                   10                  15

Val Asp

<210> SEQ ID NO 39
<211> LENGTH: 18
<212> TYPE: PRT
<213> ORGANISM: Artificial Sequence
<220> FEATURE:
<223> OTHER INFORMATION: YAP1h-S2

<400> SEQUENCE: 39

Lys Thr Ala Asn Val Pro Gln Thr Val Pro Met Arg Leu Arg Lys Leu
1               5                   10                  15

Pro Asp

<210> SEQ ID NO 40
<211> LENGTH: 26
<212> TYPE: PRT
<213> ORGANISM: Artificial Sequence
<220> FEATURE:
<223> OTHER INFORMATION: TEAD2h-S2

<400> SEQUENCE: 40

Pro Pro His Ala Phe Phe Leu Val Lys Phe Trp Ala Asp Leu Asn Trp
1               5                   10                  15

Gly Pro Ser Gly Glu Glu Ala Gly Ala Gly
            20                  25

<210> SEQ ID NO 41
<211> LENGTH: 18
<212> TYPE: PRT
<213> ORGANISM: Artificial Sequence
<220> FEATURE:
<223> OTHER INFORMATION: Raf1m-S1

<400> SEQUENCE: 41

Met Glu His Ile Gln Gly Ala Trp Lys Thr Ile Ser Asn Gly Phe Gly
1               5                   10                  15

Leu Lys

<210> SEQ ID NO 42
<211> LENGTH: 18
<212> TYPE: PRT
<213> ORGANISM: Artificial Sequence
<220> FEATURE:
<223> OTHER INFORMATION: Raf1h-S1

<400> SEQUENCE: 42

Met Glu His Ile Gln Gly Ala Trp Lys Thr Ile Ser Asn Gly Phe Gly
1               5                   10                  15

Phe Lys

```
<210> SEQ ID NO 43
<211> LENGTH: 15
<212> TYPE: PRT
<213> ORGANISM: Artificial Sequence
<220> FEATURE:
<223> OTHER INFORMATION: Pro-apoptotic peptide
<220> FEATURE:
<221> NAME/KEY: MISC_FEATURE
<222> LOCATION: (15)..(15)
<223> OTHER INFORMATION: Xaa at position 15 is D or DA or DAA or DAAS or
      vacant

<400> SEQUENCE: 43

His Glu His Lys Gly Lys Lys Ala Arg Leu Asp Trp Asn Thr Xaa
1               5                   10                  15

<210> SEQ ID NO 44
<211> LENGTH: 18
<212> TYPE: PRT
<213> ORGANISM: Artificial Sequence
<220> FEATURE:
<223> OTHER INFORMATION: Raf1h-S2

<400> SEQUENCE: 44

His Glu His Lys Gly Lys Lys Ala Arg Leu Asp Trp Asn Thr Asp Ala
1               5                   10                  15

Ala Ser

<210> SEQ ID NO 45
<211> LENGTH: 18
<212> TYPE: PRT
<213> ORGANISM: Artificial Sequence
<220> FEATURE:
<223> OTHER INFORMATION: Pro-apoptotic peptide
<220> FEATURE:
<221> NAME/KEY: MISC_FEATURE
<222> LOCATION: (14)..(14)
<223> OTHER INFORMATION: Xaa at position 14 is R or K
<220> FEATURE:
<221> NAME/KEY: MISC_FEATURE
<222> LOCATION: (16)..(16)
<223> OTHER INFORMATION: Xaa at position 16 is R or K
<220> FEATURE:
<221> NAME/KEY: MISC_FEATURE
<222> LOCATION: (18)..(18)
<223> OTHER INFORMATION: Xaa at position 18 is vacant or is one to three
      amino acids

<400> SEQUENCE: 45

Lys Met Ser Lys Asp Gly Lys Lys Lys Lys Lys Ser Xaa Thr Xaa
1               5                   10                  15

Cys Xaa

<210> SEQ ID NO 46
<211> LENGTH: 20
<212> TYPE: PRT
<213> ORGANISM: Artificial Sequence
<220> FEATURE:
<223> OTHER INFORMATION: Pro-apoptotic peptide

<400> SEQUENCE: 46

Lys Met Ser Lys Asp Gly Lys Lys Lys Lys Lys Ser Arg Thr Arg
1               5                   10                  15

Cys Thr Val Met
            20

<210> SEQ ID NO 47
```

```
<211> LENGTH: 20
<212> TYPE: PRT
<213> ORGANISM: Artificial Sequence
<220> FEATURE:
<223> OTHER INFORMATION: KRash-S1

<400> SEQUENCE: 47

Lys Met Ser Lys Asp Gly Lys Lys Lys Lys Lys Ser Lys Thr Lys
1               5                   10                  15

Cys Val Ile Met
            20

<210> SEQ ID NO 48
<211> LENGTH: 30
<212> TYPE: PRT
<213> ORGANISM: Artificial Sequence
<220> FEATURE:
<223> OTHER INFORMATION: Mut3DPT-PP2A/SET

<400> SEQUENCE: 48

Val Lys Lys Lys Lys Ile Lys Ala Glu Ile Lys Ile Glu Thr Val Thr
1               5                   10                  15

Leu Leu Val Ala Leu Lys Val Arg Tyr Arg Glu Arg Ile Thr
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Mut4DPT-PP2A/SET

<400> SEQUENCE: 49

Val Lys Lys Trp Lys Ile Lys Trp Trp Ile Lys Ile Glu Thr Val Thr
1               5                   10                  15

Leu Leu Val Ala Leu Lys Val Arg Tyr Arg Glu Arg Ile Thr
            20                  25                  30

<210> SEQ ID NO 50
<211> LENGTH: 29
<212> TYPE: PRT
<213> ORGANISM: Artificial Sequence
<220> FEATURE:
<223> OTHER INFORMATION: Mut5DPT-PP2A/SET

<400> SEQUENCE: 50

Lys Lys Trp Lys Lys Trp Lys Lys Trp Lys Lys Glu Thr Val Thr Leu
1               5                   10                  15

Leu Val Ala Leu Lys Val Arg Tyr Arg Glu Arg Ile Thr
            20                  25

<210> SEQ ID NO 51
<211> LENGTH: 30
<212> TYPE: PRT
<213> ORGANISM: Artificial Sequence
<220> FEATURE:
<223> OTHER INFORMATION: Mut3DPT-TEAD

<400> SEQUENCE: 51

Val Lys Lys Lys Lys Ile Lys Ala Glu Ile Lys Ile Arg Leu Gln Leu
1               5                   10                  15

Val Glu Phe Ser Ala Phe Val Glu Pro Pro Asp Ala Val Asp
            20                  25                  30
```